United States Patent [19]

Irmscher et al.

[11] Patent Number: 4,680,288
[45] Date of Patent: Jul. 14, 1987

[54] SULFUR-CONTAINING 6-KETOPROSTAGLANDINS

[75] Inventors: Klaus Irmscher, Darmstadt-Eberstadt; Hans-Eckart Radunz, Mühltal; Ernst Schulze; Bernhard Riefling, both of Darmstadt, all of Fed. Rep. of Germany

[73] Assignee: Merck Patent Gesellschaft mit beschrankter Haftung, Darmstadt, Fed. Rep. of Germany

[21] Appl. No.: 692,490

[22] Filed: Jan. 18, 1985

[30] Foreign Application Priority Data

Jan. 18, 1984 [DE] Fed. Rep. of Germany ....... 3401542

[51] Int. Cl.$^4$ .................. C07C 177/00; A61K 31/557
[52] U.S. Cl. ..................................... 514/63; 514/277; 514/438; 514/461; 514/530; 514/570; 514/573; 546/342; 549/79; 549/473; 556/441; 560/9; 560/118; 560/121; 562/426; 562/500; 562/503
[58] Field of Search ........................... 560/121, 9, 118; 562/503, 500, 426; 556/441; 549/79, 473; 546/342; 514/63, 277, 438, 461, 530, 570, 573

[56] References Cited

U.S. PATENT DOCUMENTS

| 4,080,458 | 3/1978 | Radunz et al. | 560/121 |
| 4,205,178 | 5/1980 | Axon | 560/121 |
| 4,210,651 | 7/1980 | Radunz et al. | 560/121 |

Primary Examiner—Robert Gerstl
Attorney, Agent, or Firm—Millen & White

[57] ABSTRACT

Sulfur-containing 6-ketoprostaglandins of the formula I

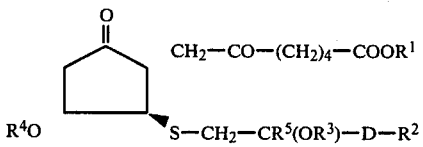

in which

D is a bond, alkylene having 1-3 C atoms, cis-alkenylene having 2-5 C atoms or alkinylene having 2-5 C atoms, $R^1$ is H, alkyl having 1-4 C atoms, aryl having 6-12 C atoms or $-C_6H_4NHCOC_6H_5$, $R^2$ is alkyl having 1-7 C atoms, alkyl having 1-7 C atoms which is substituted by halogen, cycloalkyl having 5-6 C atoms, cycloalkyl having 5-6 C atoms which is substituted by alkyl having 1-4 C atoms, phenyl, phenyl which is substituted by F, Cl, Br, alkyl having 1-4 C atoms, OH, OCH$_3$ or CF$_3$, pyridyl, naphthyl, thienyl or, if D is alkylene having 1-3 C atoms, also is alkoxy having 1-4 C atoms, alkylthio having 1-4 C atoms, phenoxy or phenoxy which is substituted by F, Cl, Br, alkyl having 1-4 C atoms, OH, OCH$_3$ or CF$_3$, $R^3$ and $R^4$ each are H, alkyl having 1-7 C atoms, tetrahydro-2-pyranyl, trialkylsilyl having a total of 3-12 C atoms, aryldialkylsilyl having a total of 8-18 C atoms, alkoxymethyl having 2-5 C atoms, aryloxymethyl having 7-11 C atoms or acyl having 1-10 C atoms, and $R^5$ is H or alkyl having 1-3 C atoms, and .... indicates that this bond is α, ━ indicates that this bond is β, and, where $R_1$ is H, their salts, show effects on the circulation, in particular hypotensive effects, as well as effects on the force of myocardial contraction.

19 Claims, No Drawings

SULFUR-CONTAINING 6-KETOPROSTAGLANDINS

BACKGROUND OF THE INVENTION

For some time, compounds which may be comprised by the term "prostacyclins" have attracted pharmacological and medical interest. Prostacyclin, or $PGI_2$, which is a recently isolated natural material belonging to the family of prostaglandins, is distinguished by pronounced properties of inhibiting platelet aggregation (The Lancet 1977, 18). The physiological effects of prostaglandins and prostacyclins are, however, both in vitro and in the mammalian body, of short duration since they are rapidly converted into pharmacologically inactive metabolites. Furthermore, it is a disadvantage that these compounds have, in addition to the desired physiological effect, at the same time a number of undesired physiological side effects which greatly restrict their use as medicaments.

SUMMARY OF THE INVENTION

Thus, it is an object of this invention to provide new compounds which have selective pharmacological effects and can be used for the preparation of medicaments.

Upon further study of the specification and appended claims, further objects and advantages of this invention will become apparent to those skilled in the art.

These objects have been achieved by providing 6-ketoprostaglandins of formula I

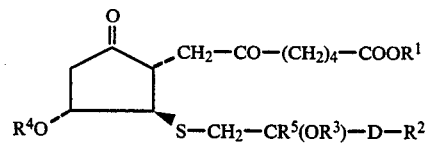

I in which

D is a bond, alkylene having 1–3 C atoms, cis-alkenylene having 2–5 C atoms or alkinylene having 2–5 C atoms, $R^1$ is H, alkyl having 1–4 C atoms, aryl having 6–12 C atoms or —$C_6H_4NHCOC_6H_5$, $R^2$ is alkyl having 1–7 C atoms, alkyl having 1–7 C atoms which is substituted by halogen, cycloalkyl having 5–6 C atoms, cycloalkyl having 5–6 C atoms which is substituted by alkyl having 1–4 C atoms, phenyl, phenyl which is substituted by F, Cl, Br, alkyl having 1–4 C atoms, OH, $OCH_3$ or $CF_3$, pyridyl, naphthyl, thienyl or, if D is alkylene having 1–3 C atoms, also is alkoxy having 1–4 C atoms, alkylthio having 1–4 C atoms, phenoxy or phenoxy which is substituted by F, Cl, Br, alkyl having 1–4 C atoms, OH, $OCH_3$ or $CF_3$, $R^3$ and $R^4$ each are H, alkyl having 1–7 C atoms, tetrahydro-2-pyranyl, trialkylsilyl having a total of 3–12 C atoms, aryldialkylsilyl having a total of 8–18 C atoms, alkoxymethyl having 2–5 C atoms, aryloxymethyl having 7–11 C atoms or acyl having 1–10 C atoms, and $R^5$ is H or alkyl having 1–3 C atoms, and . . . indicates that this bond is α, ━ indicates that this bond is β, and, where $R^1$ is H, their salts.

DETAILED DISCUSSION

It has been found that the compounds of the general formula I and their physiologically acceptable salts are well tolerated and have valuable pharmacological properties. Thus, for example, they show effects on the circulation, in particular hypotensive effects, as well as effects on the force of myocardial contraction (a positive inotropic solvent), but they also show effects inhibiting platelet aggregation.

For example, the substances on oral administration reduce, in a dose-dependent and sustained manner, the blood pressure of both normotensive anaesthetised dogs and conscious dogs with renal hypertension (for methods, see. B. A. SCHÖLKENS et al., Prostaglandins, Leukotrienes and Medicine, 10, 231–256, 1983).

The effect inhibiting platelet aggregation can be demonstrated by, for example, the in vitro aggregation test of G. V. R. BORN (Nature 194, 927–929, 1962) and by the in vivo laser-induced thrombosis test on mesenteric vessels of rats and rabbits (methods based on J. KOVACZ (Microvascular Research 6, 194, 1973) and J. DUHAULT (Arzneimittelforschung/Drug Research 22/10, 1686–1690, 1972)).

The effect on the heart can be detected in, for example, anaesthetised or conscious dogs, cats, monkeys or minipigs as well as on isolated heart preparations (for example atrium, papillary muscle or perfused whole heart) of guinea pigs or cats, for example by methods as described in Arzneimittelforschung, 31 (I) No. 1a (1981), pages 141 to 170.

Furthermore, the compounds of the formula I have cytoprotective actions on various organs of the human or animal body. Thus, for example, in the stomach they inhibit the secretion of acid much more strongly than does $PGE_2$ (on intravenous administration) and they protect the mucosa against the effect of substances which act to produce ulcers, such as alcohol, acetylsalicylic acid or taurocholic acid. They protect the liver against toxic effects, for example of $CCl_4$ or paracetamol, and they increase the chances of survival from fulminant hepatic insufficiency. In myocardial infarction, they protect against necrosis of the tissue of the heart; they diminish the size of the infarct and reduce the healing time. It is possible to treat Prinzmetal angina with substances of the formula I. They also reveal beneficial effects in the brain, for example when ischaemia has occurred. In the lung, they bring about a decrease in the vascular resistance of the central airways; thus they can be used for the treatment of asthmatic diseases.

In addition, the 6-ketoprostaglandins of the formula I have vasodilator, diuretic and bronchospasmolytic properties, and they inhibit the secretion of gastric juice, the degradation of lipids and the release of noradrenalin and they reduce the swelling of nasal mucosa, which likewise can be demonstrated by methods customary for this purpose. Furthermore, the 6-ketoprostaglandins of the general formula I can also affect the function of the corpus luteum, the transport of ova through the fallopian tube, and nidation and fertility.

The compounds of the general formula I and their physiologically acceptable salts can thus be used as active compounds in medicaments in human and veterinary medicine as well as intermediates for the preparation of other active compounds for medicaments.

In the general formula I and the other formulae in this application, an α bond is drawn as a dotted line and a β bond is drawn as a thin wedge. Bonds which may be α or β are indicated by a wavy line. Those compounds in which the R³O group in the thioether side chain is α, and the group R⁵ is β are preferred.

The compounds of the general formula I contain three asymmetric C atoms in the five-membered carbocyclic ring. Other centers of asymmetry may occur in the thioether side chain.

Thus, the compounds of the general formula I may occur in a large number of stereoisomeric forms.

In addition to the individual racemeates and racemic mixtures, the invention also relates to the various optically active isomers of the general formula I.

The invention also relates to a process for the preparation of the compounds of the general formula I, and of their salts, which is characterized in that a compound of the formula II

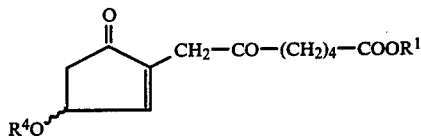

in which $R^1$ and $R^4$ have the meanings indicated above, is reacted with a compound of the formula III

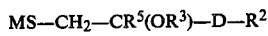

$$MS-CH_2-CR^5(OR^3)-D-R^2 \qquad III$$

in which M is H or one equivalent of a cation, and D, $R^2$, $R^3$ and $R^5$ have the meanings indicated above, and/or in that, where appropriate, a compound of the formula I, in which $R^1$ and/or $R^3$ and/or $R^4$ differ(s) from H, is converted, by treatment with solvolyzing agents, into a compound of the formula I, in which $R^1$ and/or $R^3$ and/or $R^4$ is (are) H, and/or a compound of the formula I, in which $R^1$ is H, is esterified and/or a compound of the formula I, in which $R^3$ and/or $R^4$ is (are) H, is etherified or esterified and/or a compound of the formula I which is obtained as a racemate is resolved into its enantiomers and/or a compound of the formula I, in which $R^1$ is H, is converted into one of its salts by reaction with a base.

In formulae I and III, D is preferably a bond and alkylene having 1, 2 or 3 C atoms, in particular methylene, but also ethylene, propylene or 1-methylethylene. When D is cis-alkenylene having 2–5 C atoms, then unbranched cis-alkenylene groups having 3, 4 or 5 C atoms are preferred, in particular cis-but-2-enylene. However, D can also be a branched cis-alkenylene group, for example 1-methylbut-2-enylene. When D is alkinylene having 2–5 C atoms, then branched alkinylene groups having 3, 4 or 5 C atoms are preferred, in particular 1-pentin-1,4-ylene.

The group $R^5$ is hydrogen or methyl in particular.

$R^1$ is hydrogen in particular, also an alkyl radical, preferably an unbranched alkyl radical having up to 4 C atoms, such as methyl, ethyl, propyl or n-butyl, but it is also a branched radical, such as isopropyl or tert.-butyl. Moreover, $R^1$ is an aryl radical having 6–12 C atoms, such as phenyl, tolyl, biphenylyl or naphthyl. In addition, $R^1$ is particularly advantageously the radical —C₆H₄—NH—CO—C₆H₅.

$R^2$ is, for example, an alkyl radical having 1–7 C atoms, preferably an unbranched alkyl radical having 1–7 C atoms, such as methyl, ethyl, propyl, butyl, pentyl, hexyl or heptyl. However, $R^2$ can also be a branched alkyl radical having 3–7 C atoms, such as, for example, 1-methylpentyl, 1,1-dimethylpentyl, 2-methylpentyl, 3-methylpentyl, 3,3-dimethylpentyl, 4-methylpentyl or 1-methylhexyl.

When $R^2$ is an alkyl radical having 1–7 C atoms which is substituted by halogen, then the halogen substituent, which is preferably fluorine or chlorine, but can also be bromine or iodine, is located in particular in the terminal position. Examples which may be mentioned are: chloromethyl, 2-chloroethyl, 3-chloropropyl, 4-chlorobutyl, 5-chloropentyl, 1-methyl-4-chlorobutyl, 1-methyl-5-chloropentyl, 1,1-dimethyl-4-chlorobutyl, fluoromethyl, 2-fluoroethyl, 3-fluoropropyl, 4-fluorobutyl, 5-fluoropentyl; 4-bromobutyl, 5-bromobutyl.

In addition, $R^2$ is preferably cycloalkyl having 5–6 C atoms, such as cyclopentyl and, in particular, cyclohexyl. Furthermore, $R^2$ can be cycloalkyl having 5–6 C atoms which is substituted by alkyl having 1–4 C atoms, preferably 1–2 C atoms, such as, for example, 2-methylcyclohexyl, 3-methylcyclohexyl, 4-methylcyclohexyl, 4-ethylcyclohexyl, 4-propylcyclohexyl, 4-isopropylcyclohexyl, 4-butylcyclohexyl, 4-tert.-butylcyclohexyl; 2-methylcyclopentyl, 3-methylcyclopentyl, 3-ethylcyclopentyl, 3-propylcyclopentyl, 3-butylcyclopentyl.

In addition, $R^2$ is preferably phenyl or phenyl which is substituted once, twice or three times by F, Cl, Br, alkyl having 1–4 C atoms, OH, OCH₃ or CF₃. When $R^2$ is a substituted phenyl radical, then it is preferably substituted once, the substituent being located in the 2-, 3- or 4-position.

Thus, $R^2$ is preferably also phenyl, 3-fluorophenyl, 4-fluorophenyl, 2-chlorophenyl, 3-chlorophenyl, 4-chlorophenyl, 3-bromophenyl, 4-bromophenyl, 2-tolyl, 3-tolyl, 4-tolyl, 4-ethylphenyl, 4-isopropylphenyl, 4-butylphenyl, 3-hydroxyphenyl, 4-hydroxyphenyl, 3-methoxyphenyl, 4-methoxyphenyl, 2-trifluoromethylphenyl, 3-trifluoromethylphenyl, 4-trifluoromethylphenyl, but it is also, for example 2,4-dichloro-, 3,4-dichloro-, 2,4-dimethyl-, 3,4-dimethyl-, 2,4-dimethoxy-, 2,3-dimethoxy-, 2,4,6-trimethyl- or 3,4,5-trimethoxyphenyl.

Furthermore, $R^2$ is 2-pyridyl, 3-pyridyl, 4-pyridyl, 1-naphthyl, 2-naphthyl, 2-thienyl or 3-thienyl.

When D is alkylene having 1–3 C atoms, in particular methylene, then $R^2$ is also preferably alkoxy having 1–4 C atoms, such as methoxy, ethoxy, propyloxy or butyloxy; alkylthio having 1–4 C atoms, such as methylthio, ethylthio, propylthio or butylthio; phenoxy or phenoxy which is substituted once, twice or three times by F, Cl, Br, alkyl having 1–4 C atoms, OH, OCH₃ or CF₃. When $R^2$ is a substituted phenoxy radical, then it is preferably substituted once, the substituent being located in the 2-position but, in particular, in the 3- or 4-position. Examples of such radicals are phenoxy, 3-fluorophenoxy, 4-fluorophenoxy, 3-chlorophenoxy, 4-chlorophenoxy, 3-bromophenoxy, 4-bromophenoxy, 2-methylphenoxy, 3-methylphenoxy, 4-methylphenoxy, 4-ethylphenoxy, 4-isopropylphenoxy, 4-butylphenoxy, 3-hydroxyphenoxy, 4-hydroxyphenoxy, 3-methoxyphenoxy, 4-methoxyphenoxy, 3-trifluoromethylphenoxy, 4-trifluoromethylphenoxy, but it is also, for example, 2,4-dichloro-, 3,4-dichloro-, 2,4-dimethyl-, 3,4-dimethyl-, 2,4-dimethoxy-, 2,3-dimethoxy-, 2,4,6-trimethyl- or 3,4,5-trimethoxyphenoxy.

Accordingly, D—$R^2$ is preferably butyl, pentyl, hexyl, heptyl, octyl, nonyl, decyl; 1-methylpentyl, 1,1-dimethylpentyl, 2-methylpentyl, 3-methylpentyl, 4-methylpentyl, 1-methylhexyl; 4-chlorobutyl, 4-chloropentyl, 5-chloropentyl, 1-methyl-4-chlorobutyl, 1,1-dimethyl-4-chlorobutyl, 5-fluoropentyl, 5-bromopentyl; but-2-enyl, pent-2-enyl, hex-2-enyl, pent-3-enyl, hex-3-enyl, hex-4-enyl, hept-4-enyl; 1-methylpent-3-inyl; cyclopentyl, cyclohexyl, 3-methylcyclohexyl, 4-methylcyclohexyl, 3-ethylcyclohexyl, 4-isopropylcyclohexyl, cyclohexylmethyl, 2-cyclohexylethyl, cyclopentylmethyl; phenyl, 2-fluorophenyl, 3-fluorophenyl, 4-fluorophenyl, 2-chlorophenyl, 3-chlorophenyl, 4-chlorophenyl, 2-tolyl, 3-tolyl, 4-tolyl, 3-methoxyphenyl, 4-methoxyphenyl, 2-trifluoromethylphenyl, 3-trifluoromethylphenyl, 4-trifluoromethylphenyl; benzyl, 4-fluorobenzyl, 3-chlorobenzyl, 4-chlorobenzyl, 4-methylbenzyl, 4-methoxybenzyl, 3-trifluoromethylbenzyl, 4-trifluoromethylbenzyl; 2-phenylethyl, 2-(3-chlorophenyl)ethyl, 2-(3-trifluoromethylphenyl)ethyl; 4-pyridyl, 4-pyridylmethyl, 2-naphthyl, 2-naphthylmethyl, 2-thienyl, 2-thienylmethyl, 3-thienyl, 3-thienylmethyl; ethoxymethyl, propyloxymethyl, butyloxymethyl, 2-methoxyethyl, 2-ethoxyethyl, 2-propyloxyethyl, 3-methoxpropyl, 3-ethoxypropyl; ethylthiomethyl, propylthiomethyl, butylthiomethyl, 2-methylthiomethyl, 2-ethylthioethyl, 2-propylthioethyl, 3-methylthiopropyl, 3-ethylthiopropyl; phenoxymethyl, 3-fluorophenoxymethyl, 4-fluorophenoxymethyl, 3-chlorophenoxymethyl, 4-chlorophenoxymethyl, 4-methoxyphenoxymethyl, 3-trifluoromethylphenoxymethyl, 4-trifluoromethylphenoxymethyl.

The radicals $R^3$ and $R^4$ are preferably H. In addition, these two radicals, but in particular the radical $R^3$, can be hydroxyl-protective groups, in particular alkyl having 1–7 C atoms, preferably tert.-butyl, methyl, ethyl or propyl, also isopropyl, butyl, isobutyl, sec.-butyl, pentyl, hexyl or heptyl; tetrahydro-2-pyranyl; trialkylsilyl having a total of 3–2 C atoms, preferably trimethylsilyl, tert.-butyldimethylsilyl, triethylsilyl, triisopropylsilyl, di-tert.-butylmethylsilyl; aryldialkylsilyl having a total of 8–18 C atoms, preferably phenyldimethylsilyl; alkoxymethyl having 2–5 C atoms, such as methoxymethyl, ethoxymethyl, tert.-butoxymethyl; aryloxymethyl having 7–11 C atoms, such as phenoxymethyl; acyl having 1–10 C atoms, in particular alkanoyl having 1–6 C atoms, such as formyl, acetyl, trimethylacetyl, tert.-butylacetyl, or aroyl having 7–10 C atoms, such as benzoyl, also carbonic ester groups, e.g., $C_{1-7}$-alkoxycarbonyl, e.g., oxycarbonyl or $C_{7-11}$-aralkoxycarbonyl, e.g., benzyloxycarbonyl.

Suitable salts of the compounds of the formula I are preferably physiologically acceptable metal and ammonium salts, in particular the sodium, potassium, magnesium, calcium and ammonium salts, also substituted ammonium salts, such as, for example, the monoethanolammonium and triethanolammonium, cyclohexylammonium and dibenzylethylenediammonium salts.

Accordingly, the invention relates in particular to those compounds of the general formula I in which at least one of the radicals mentioned has one of the meanings indicated above, in particular the preferred meanings indicated above. Some preferred groups of compounds can be expressed by the following part formulae Ia to Ij, which correspond to the general formula I but in which in Ia
D is a bond or —$CH_2$—;
in Ib
$R^1$ is H, methyl, ethyl or —$C_6H_4$—NH—CO—$C_6H_5$;
in Ic
$R^2$ is alkyl having 1–6 C atoms, cyclohexyl, phenyl, phenyl which is substituted by F, Cl, $CH_3$, $OCH_3$ or $CF_3$, or naphthyl;
in Id
$R^3$ is H and
$R^4$ is H, tert.-butyl, tert.-butoxymethyl, tetrahydro-2-pyranyl, trialkylsilyl having a total of 3–6 C atoms, or alkanoyl having 2–6 C atoms;
in Ie
D is a bond, —$CH_2$— or 1-pentin-1,4-ylene,
$R^1$ is H or benzamidophenyl,
$R^2$ is alkyl having 1–7 C atoms, phenyl, chlorophenyl or, when D is —$CH_2$—, also chlorophenoxy,
$R^3$ is H,
$R^4$ is H, tert.-butyl, tert.-butoxymethyl, tetrahydro-2-pyranyl, trialkylsilyl having a total of 3–6 C atoms, or alkanoyl having 2–6 C atoms, and
$R^5$ is H or $CH_3$;
in If
D is a bond, —$CH_2$— or 1-pentin-1,4-ylene,
$R^1$ is H or p-benzamidophenyl,
$R^2$ is methyl, pentyl, hexyl, 1-methylpentyl, 1-methylhexyl, phenyl, o-chlorophenyl or, when D is —$CH_2$—, is also m-chlorophenoxy,
$R^3$ is H,
$R^4$ is H or tert.-butyldimethylsilyl, and
$R^5$ is H or $CH_3$;
in Ig
D is a bond,
$R^1$ is H or p-benzamidophenyl,
$R^2$ is pentyl, hexyl, 1-methylpentyl or 1-methylhexyl,
$R^3$ is H,
$R^4$ is H or tert.-butyldimethylsilyl, and
$R^5$ is H or $CH_3$;
in Ih
D is a bond or —$CH_2$—,
$R^1$ is H or p-benzamidophenyl,
$R^2$ is phenyl, o-chlorophenyl or, when D is —$CH_2$—, is also m-chlorophenoxy,
$R^3$ is H,
$R^4$ is H or tert.-butyldimethylsilyl, and
$R^5$ is H or $CH_3$;
in Ii
D is a bond,
$R^1$ is H or p-benzamidophenyl,
$R^2$ is 1-methylhexyl,
$R^3$ is H,
$R^4$ is H, tert.-butoxymethyl, tetrahydro-2-pyranyl, trialkylsilyl having a total of 3–6 C atoms, or alkanoyl having 2–6 C atoms, and
$R^5$ is H;
in Ij
D is a bond,
$R^1$ is H or p-benzamidophenyl,
$R^2$ is 1-methylhexyl,
$R^3$ is H,
$R^4$ is H or tert.-butyldimethylsilyl, and
$R^5$ is H.

Otherwise, the preparation of the compounds of the general formula I is carried out by methods known per se, as described in the literature (for example in the standard works, such as Houben-Weyl, Methoden der Organischen Chemie (Methods of Organic Chemistry) published by George Thieme, Stuttgart; Organic Reactions, John Wiley & Sons, Inc., New York), namely under reaction conditions as are known and suitable for the reactions mentioned. This can also entail use being made of variants which are known per se but which are not mentioned here in detail.

The starting materials, in particular those of the general formulae II and III, can, if desired, also be formed in situ, in such a manner that they are not isolated from the reaction mixture but are immediately reacted further to give the compounds of the general formula I.

The reaction of a compound of the formula II with a thiol or thiolate of the formula III is, as a rule, carried out in the presence of a basic catalyst and in the presence or absence of an inert solvent, at temperatures between about −50° and +20°, preferably between −30° and 0°.

Suitable solvents which are preferred are alcohols, such as methanol, ethanol, propanol, isopropanol, butanol, tert.-butyl alcohol, amyl alcohol, 2-methoxyethanol or 2-ethoxyethanol; ethers, such as diethyl ether, tetrahydrofuran (THF), dioxane or ethylene glycol dimethyl ether, chlorinated hydrocarbons, such as methylene chloride or chloroform; or water.

Examples of suitable basic catalysts are alkali metal or alkaline earth metal hydroxides, such as NaOH, KOH or Ca(OH)$_2$; alkali metal alcoholates, such as NaOCH$_3$, NaOC$_2$H$_5$ or KO-tert.-C$_4$H$_9$; basic salts, preferably carbonates or acetates, such as K$_2$CO$_3$ or NaOCOCH$_3$; ammonia; amines, preferably secondary or tertiary amines, such as triethylamine, diisopropylamine, dicyclohexylamine, dimethylaniline, piperidine, 2,6-dimethylpiperidine, 2,2,6,6-tetramethylpiperidine, pyrrolidine, pyridine, quinoline, diazabicyclo[2.2.2]octane or diazabicyclo[3.4.0]nonene; but also primary amines, such as tert.-butylamine or cyclohexylamine; or quaternary ammonium hydroxides, such as tetramethylammonium hydroxide or, in particular, benzyltrimethylammonium hydroxide. It is also possoble to use one of the amines mentioned, in particular a secondary or tertiary amine, at the same time as the solvent, and thus to work in the absence of the inert solvents mentioned. It is particularly preferable to work under an inert gas atmosphere, for example under nitrogen.

Compounds of the formula I or compounds which correspond to the formula I, in which R$^1$ and/or R$^3$ and/or R$^4$ differ(s) from H, can be converted, by treatment with solvolyzing agents, preferably under neutral or acid conditions, into compounds of the formula I in which R$^1$ and/or R$^4$ and/or R$^4$ is (are) H.

The solvolyzing agents which are preferably used are hydrolyzing agents, such as water or water mixed with organic solvents, in the absence or preferably in the presence, of an acid catalyst. Examples of suitable organic solvents are alcohols, such as methanol, ethanol, propanol, isopropanol, butanol, tert.-butyl alcohol, amyl alcohol, 2-methoxyethanol or 2-ethoxyethanol; ethers, such as diethyl ether, THF, dioxane or ethylene glycol dimethyl ether, acids, such as formic acid, acetic acid, propionic acid or butyric acid; esters, such as ethyl acetate or butyl acetate; ketones, such as acetone; amides, such as dimethylformamide (DMF) or phosphoric hexamethyltriamide; nitriles, such as acetonitrile; sulfoxides, such as dimethyl sulfoxide (DMSO); sulfones, such as tetrahydrothiophene S,S-dioxide; and mixtures of these solvents with one another and/or with water.

Examples of suitable acid catalysts for solvolysis are inorganic acids, for example hydrochloric acid, sulfuric acid, phosphoric acid, hydrofluoric acid, hydrobromic acid, or strong organic acids, such as chloroacetic acid, trichloroacetic or trifluoroacetic acid, methane-, ethane-, benzene- or p-toluenesulfonic acid. The basic catalysts which are preferably used are alkali metal or alkaline earth metal hydroxides, such as sodium, potassium or calcium hydroxide, or basic salts, such as sodium or potassium carbonate. It is also possible to use organic bases, for example ethylamine, diethylamine, triethylamine, isopropylamine, n-butylamine or tri-n-butylamine, diemthylaniline, pyrrolidine, piperidine, morpholine, pyridine, α-picoline or quinoline, or quaternary ammonium hydroxides, such as, for example, tetramethylammonium hydroxide or benzyltrimethylammonium hydroxide as basic catalysts. It is also possible to use an excess of the catalyst in place of a solvent. The solvolysis is preferably carried out at temperatures between about −50° and 20°, preferably between −15° and 0°.

In particular, it is also possible to convert esters of the formula I (R$^1$≠H) by hydrolysis into acids of the formula I (R$^1$=H), for example by basic hydrolysis as indicated above, preferably under mild conditions. Enzymatic cleavage of the esters is also possible, for example using a lipase in aqueous suspension at about 0°–30°.

Furthermore, it is possible to convert, in particular, silyl ethers of the formula I (R$^3$ and/or R$^4$=trialkylsilyl or aryldialkylsilyl) by hydrolysis into the corresponding free alcohols of the formula I (R$^3$ and/or R$^4$=H), preferably using HF in aqueous acetonitrile at temperatures between about 0° and 30°.

An acid of the formula I (R$^1$=H) can be converted by reaction with an appropriate esterifying agent into an ester of the formula I (R$^1$=alkyl having 1-4 C atoms, aryl having 6-12 C atoms or —C$_6$H$_4$NH—CO—C$_6$H$_5$). Examples of esterifying agents are alcohols having up to 4 C atoms, preferably in the presence of an inorganic or organic acid, such as HCl, HBr, HI, H$_2$SO$_4$, H$_3$PO$_4$, trifluoroacetic acid, a sulfonic acid, such as benzenesulfonic acid or p-toluenesulfonic acid, or a acid ion exchanger; diazoalkanes having up to 4 C atoms, preferably diazomethane; olefins (for example isobutylene), preferably in the presence of acid catalysts (for example ZnCl$_2$, BF$_3$, H$_2$SO$_4$, arylsulfonic acid, pyrophosphoric acid, boric acid, oxalic acid); alkyl halides having up to 4 C atoms, preferably bromides, such as ethyl, propyl, isopropyl or butyl bromide, but also the corresponding chlorides or iodides; alkyl carboxylates or sulfonates, it being possible for the acid radical to be arbitrary and the alkyl radical to contain up to 4 C atoms, preferably methyl, ethyl, propyl, isopropyl or butyl acetate, formate, methylsulfonate, ethylsulfonate or p-toluenesulfonate, and, in particular, also dialkyl sulfates having up to 4 C atoms, such as dimethyl sulfate or diethyl sulfate.

The esterification is preferably carried out in an inert, preferably anhydrous solvent, for example an ether, such as diethyl ether or THF, an alcohol, preferably one of the alcohols having up to 4 C atoms mentioned, or in a hydrocarbon, such as petroleum ether, hexane, benzene or toluene, or in mixtures of these solvents, at temperatures between −10° and 40°, preferably at room temperature. As a rule, the reaction times are between 30 minutes and 20 hours.

Aromatic esters of the formula I (R$^1$=aryl having 6–12 C atoms or —C$_6$H$_4$—NH—CO—C$_6$H$_5$) can be prepared from acids of the formula I (R$^1$=H) by reaction with a phenol (such as, for example, phenol, m-cresol, p-cresol, p-ethylphenol, β-naphthol, p-phenylphenol) or a compound of the formula HO—C$_6$H$_4$—NH—CO—C$_6$H$_5$. The latter compounds are known, for example from German Offenlegungsschrift No. 2,644,972.

The esterification of an acid of the formula I ($R^1=H$) with a phenol can be carried out by methods known per se; it is preferably carried out in the presence of a water-binding agent, for example a carbodiimide, such as dicyclohexylcarbodiimide, and in an inert organic solvent, preferably an ether, such as diethyl ether, 1,2-dimethoxyethane, THF or dioxane; or a halogenated hydrocarbon, such as methylene chloride or 1,2-dichloroethane; or in mixtures of these solvents with DMF. The reaction temperatures are preferably between, for example, about $-20°$ and 100°.

In an analogous manner, compounds of the formula I in which $R^3$ and/or $R^4$ is (are) H can be esterified with an acid which contains 1–10 C atoms, or with a reactive derivative of an acid of this type. Examples of suitable reactive acid derivatives are the anhydrides and the halides, for example chlorides or bromides of the acids.

Thus, for example, it is possible to acylate the hydroxy compounds of the formula I by treatment with excess anhydride, for example acetic anhydride, in the presence of a base, such as triethylamine, imidazole or pyridine, at temperatures between about $-20°$ and 50°, preferably between 0° and 30°. In this, secondary OH groups are preferentially esterified before tertiary.

In a similar manner, it is possible to etherify the hydroxy compounds of the formula I ($R^3$ and/or $R^4=H$) using appropriate alkyl, trialkylsilyl, aryldialkylsilyl, alkoxymethyl or aryloxymethyl halides, preferably chlorides, advantageously in the presence of an inert solvent, such as DMF.

The compounds of the formula I are usually obtained as mixtures of various stereoisomeric forms, that is to say as mixtures of racemates as a rule. Racemates can be isolated from the racemate mixtures and obtained pure by, for example, recrystallization of the compounds themselves or of readily crystallizable derivatives, but in particular by means of chromatographic methods, both adsorption chromatographic or partition chromatographic methods and mixed types being suitable.

The racemates can be separated into their optical antipodes by known methods as are indicated in the literature. The method of chemical separation is preferred.

Thus, an optically active base can be reacted with the carboxyl group of a compound of the formula I ($R^1=H$). For example, it is possible to form the diastereomeric salts with optically active amines, such as quinine, cinchonidine, brucine, cinchonine, hydroxyhydrindamine, morphine, 1-phenylethylamine, 1-naphthylethylamine, phenoxynaphthylmethylamine, quinidine, strychnine, basic aminoacids, such as lysine, arginine or esters of amino-acids. In a similar manner, diastereomeric esters can be prepared by esterification of carboxylic acids of the formula I ($R^1=H$) with optically active alcohols, such as borneol, menthol, 2-octanol. The resulting diastereomeric salts or esters are separated by crystallization, and the optically active compounds from the mixture are liberated.

However, it is also possible to use for the formation of diastereomers the other functional groups present in the compounds of the formula I. Thus, for example, it is possible to esterify OH groups with optically active acids, such as (+)- and (−)-tartaric acid or camphoric acid, and to obtain the pure enantiomers from these derivatives.

Of course, it is also possible to obtain optically active compounds by the methods described by using starting materials which are already optically active.

In addition, it is possible to convert the free acids of the formula I ($R^1=H$) into one of their salts, in particular one of their physiologically acceptable metal or ammonium salts, by reaction with a base.

Some of the starting compounds for the preparation of the compounds of the formula I, according to the invention, by the methods described above are known, but most of them are new. New starting compounds can be prepared from known compounds in analogy to known processes, for example new compounds of the formula II as follows:

$1\alpha$-Hydroxy-$2\alpha$-(6-carboxyhex-2-enyl)-$3\alpha,4\alpha$-oxidocyclopentane, which is known from Synth. Comm. 4 (6), 317 (1974), or its esters are converted, using N-bromosuccinimide, into 1-oxa-2-(1-bromo-4-carboxybutyl)-5,6-oxidobicyclo[3.3.0]octane or its esters. Using strong bases, for example K tert.-butylate, it is possible to prepare from these 6-oxo-7-($2\alpha,3\alpha$-oxido-$5\alpha$-hydroxy-$1\alpha$-cyclopentyl)heptanoic acid or its esters. Oxidation, for example with $CrO_3$, leads to the corresponding $2\alpha,3\alpha$-oxido-5-oxo-$1\alpha$-cyclopentyl derivatives which, by cleavage of the epoxide and dehydration, provide compounds of the formula II in which $R^4$ is H. The other compounds of the formula II are accessible from these by customary etherification or esterification. The compounds of the formula III are 2-hydroxythiols or their alkali metal, alkaline earth metal or optionally substituted ammonium salts. Most of the thiols of the formula III are known, for example from German Offenlegungschrift No. 2,256,537, German Offenlegungsschrift No. 2,422,924 and German Offenlegungsschrift No. 2,644,972. New compounds of the formula III can be prepared from known compounds in analogy to known processes, for example from the corresponding oxiranes by reaction with $H_2S$ and, where appropriate, subsequent conversion into their alkali metal, alkaline earth metal or optionally substituted ammonium salts. Likewise, the oxiranes can be reacted directly with alkali metal, alkaline earth metal or ammonium bisulfides, in which case the compounds of the formula III with M not equal to H are then obtained directly.

The invention also relates to the use of the compounds of the formula I and their physiologically acceptable salts for the preparation of pharmaceutical formulations, in particular by non-chemical means. For this purpose, they can be converted into a suitable form for administration together with at least one solid, liquid and/or semi-liquid vehicle or auxiliary and, where appropriate, combined with one or more other active compound(s).

The invention also relates to agents, in particular pharmaceutical formulations, containing at least one compound of the formula I and/or one of its physiologically acceptable salts.

These formulations can be used as medicaments in human or veterinary medicine. Suitable vehicles are organic or inorganic substances which are suitable for enteral (for example oral) or parenteral administration, and with which the new compounds do not react, for example water, vegetable oils, benzyl alcohols, polyethylene glycols, glycerol triacetate, gelatine, carbohydrates, such as lactose or starch, magnesium stearate, talc, vaseline. In particular tablets, coated tablets, capsules, syrups, juices or drops are used for oral administration, suppositories for rectal administration, and solutions, preferably oily or aqueous solutions, but also suspensions, emulsions or implants for parenteral administration. It is also possible to freeze-dry the new compounds and use the resulting lyophilizates, for example, for the preparation of products for injection. The formulations indicated can be sterilized and/or contain auxiliaries, such as lubricants, preservatives, stabilisers and/or wetting agents, emulsifiers, salts to affect the osmotic pressure, buffer substances, colorants, flavorings and/or aromatics. Where desired, they can also contain one or more other active compounds, for example one or more vitamins.

The invention also relates to the use of the compounds of the formula I for combating diseases, in particular all forms of hypertension and of cardiac insufficiency, also for affecting platelet function in the sense of inhibition of aggregation (adhesion), or disorders of the atherosclerotic type.

The invention also relates to the use of the compounds of the formula I for the therapeutic treatment of the human or animal body. This entails the substances according to the invention being administered, as a rule, in analogy to known products for similar indications which are commercially available, preferably in doses between about 0.1 and 100 mg, in particular between 0.5 and 50 mg, per dosage unit. The daily dose is preferably between about 0.01 and 1 mg/kg body weight. However, the specific dose for each particular patient depends on a wide variety of factors, for example on the efficacy of the specific compound used, the age, body weight, general state of health, sex, on the diet, on the time and route of administration, on the rate of elimination, the drug combination and the severity of the particular disorder for which the therapy is applied. Oral administration is preferred. In comparison with the digitalis glycosides hitherto used for the therapy of cardiac insufficiency, the compounds of the formula I are distinguished by an improved therapeutic range, the lack of undesired side effects and peripheral relief.

In general, the compounds of this invention can be administered analogously to epoprostenol at dosages at 10-50 mcg/kg/day when applied orally.

Rf values are on silica gel with ethyl acetate as the eluting agent, unless indicated otherwise.

Without further elaboration, it is believed that one skilled in the art can, using the proceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celcius; unless otherwise indicated, all parts and percentages are by weight.

"Usual work-up" signifies: the mixture is evaporated, where appropriate under reduced pressure, water or aqueous acid and $CH_2Cl_2$ are added, the phases are separated, and the organic phase is dried with $MgSO_4$, evaporated, and the product is purified by chromatography on silica gel.

EXAMPLE 1

A solution of 32.4 g of 2-hydroxy-2-methylheptanethiol and 112 ml of diisopropylamine in 320 ml of THF is heated at 40° for 2 hours, then cooled to −25° and a precooled solution, in 450 ml of THF, of 54.9 g of p-benzamidophenyl 6-oxo-7-(3-tert.-butyldimethyl-silyloxy-5-oxo-1-cyclopentenyl)heptanoate [m.p. 136°-137°; obtainable by reaction of 2α-(6-carboxy-2-cis-hexenyl)-3α,4α-oxido-1α-cyclopentanol with N-bromosuccinimide in aqueous acetone to give 1-oxa-2-(1-bromo-4-carboxybutyl)-5,6-oxidobicyclo[3.3.0]octane, reaction with K tert.-butylate in THF to give 6-oxo-7-(2α,3α-oxido-5α-hydroxy-1α-cyclopentyl)heptanoic acid (p-benzamidophenyl ester, m.p. 134°-135°), oxidation with $CrO_3$ in aqueous acetone to give 6-oxo-7-(2α,3α-oxido-5-oxo-1α-cyclopentyl)heptanoic acid (m.p. 93°-94°; p-benzamidophenyl ester, m.p. 140°-141°), reaction with p-benzamidophenol/dicyclohexylcarbodiimide in the presence of p-toluenesulfonic acid to give p-benzamidophenyl 6-oxo-7-(3-hydroxy-5-oxo-1-cyclopentyl)heptanoate (m.p. 143°-146°) and etherification with tert.-butyldimethylchlorosilane] is added slowly. The mixture is stirred at −25° for 24 hours, then poured into ice-cold citric acid solution, worked up as usual and p-benzamidophenyl 6,9-dioxo-11α-tert.-butyldimethylsilyloxy-13-thia-15-hydroxy-15-methylprostanoate, mixture of isomers, m.p. 112°, is obtained. This mixture can be separated into the 15α and 15β isomers by chromatography.

The following p-benzamidophenyl prostanoates can be obtained analogously by addition of appropriate thiols of the formula III onto appropriate cyclopentenones:

6,9-dioxo-11α-tert.-butyldimethylsilyloxy-13-thia-15-hydroxy-, mixture of isomers, m.p. 141°-142°,
6,9-dioxo-11α-tert.-butyldimethylsilyloxy-13-thia-15α-hydroxy-, m.p. 137°-138°,
6,9-dioxo-11α-tert.-butyldimethylsilyloxy-13-thia-15β-hydroxy, m.p. 146°-147°,
6,9-dioxo-11α-tert.-butyldimethylsilyloxy-13-thia-15-hydroxy-20-methyl-, mixture of isomers, m.p. 142°-143°,
6,9-dioxo-11α-tert.-butyldimethylsilyloxy-13-thia-15α-hydroxy-20-methyl-, m.p. 135°-136°,
6,9-dioxo-11α-tert.-butyldimethylsilyloxy-13-thia-15β-hydroxy-20-methyl-, m.p. 146°,
6,9-dioxo-11α-tert.-butyldimethylsilyloxy-13-thia-15-hydroxy-16-methyl-, mixture of isomers, m.p. 125°-126°,
6,9-dioxo-11α-tert.-butyldimethylsilyloxy-13-thia-15α-hydroxy-16-methyl-, m.p. 125°-126°,
6,9-dioxo-11α-tert.-butyldimethylsilyloxy-13-thia-15β-hydroxy-16-methyl-, m.p. 132°-133°,
6,9-dioxo-11α-tert.-butyldimethylsilyloxy-13-thia-15-hydroxy-16,20-dimethyl-, mixture of isomers, m.p. 124°-125°,
6,9-dioxo-11α-tert.-butyldimethylsilyloxy-13-thia-15α-hydroxy-16,20-dimethyl-, m.p. 126°-127°,
6,9-dioxo-11α-tert.-butyldimethylsilyloxy-13-thia-15β-hydroxy-16,20-dimethyl-, m.p. 131°-132°
6,9-dioxo-11α-tert.-butyldimethylsilyloxy-13-thia-15-hydroxy-20-ethyl-, mixture of isomers, m.p. 143°
6,9-dioxo-11α-tert.-butyldimethylsilyloxy-13-thia-15α-hydroxy-20-ethyl-, m.p. 138°
6,9-dioxo-11α-tert.-butyldimethylsilyloxy-13-thia-15β-hydroxy-20-ethyl-, m.p. 147°
6,9-dioxo-11α-tert.-butyldimethylsilyloxy-13-thia-15-hydroxy-15,20-dimethyl-, mixture of isomers, m.p. 114°
6,9-dioxo-11α-tert.-butyldimethylsilyloxy-13-thia-15α-hydroxy-15,20-dimethyl-
6,9-dioxo-11α-tert.-butyldimethylsilyloxy-13-thia-15β-hydroxy-15,20-dimethyl-
6,9-dioxo-11α-tert.-butyldimethylsilyloxy-13-thia-15-hydroxy-16,16,21-trimethyl-, mixture of isomers,
6,9-dioxo-11α-tert.-butyldimethylsilyloxy-13-thia-15α-hydroxy-16,16,21-trimethyl- 6,9-dioxo-11α-tert.-butyldimethylsilyloxy-13-thia-15β-hydroxy-16,16,21-trimethyl- 6,9-dioxo-11α-tert.-butyldimethylsilyloxy-13-thia-15-hydroxy-15-methyl-20-ethyl-, mixture of isomeres, m.p. 115°

6,9-dioxo-11α-tert.-butyldimethylsilyloxy-13-thia-15α-hydroxy-15-methyl-20-ethyl- 6,9-dioxo-11α-tert.-butyldimethylsilyloxy-13-thia-15β-hydroxy-15-methyl-20-ethyl- 6,9-dioxo-11α-tert.-butyldimethylsilyloxy-13-thia-15-hydroxy-16-methyl-20-ethyl-, mixture of isomers, m.p. 128°

6,9-dioxo-11α-tert.-butyldimethylsilyloxy-13-thia-15α-hydroxy-16-methyl-20-ethyl-, m.p. 127°

6,9-dioxo-11α-tert.-butyldimethylsilyloxy-13-thia-15β-hydroxy-16-methyl-20-ethyl, m.p. 133°

6,9-dioxo-11α-tert.-butyldimethylsilyloxy-13-thia-15-hydroxy-16,17,18,19,20-pentanor-15-cyclohexyl-, mixture of isomers, m.p. 158°

6,9-dioxo-11α-tert.-butyldimethylsilyloxy-13-thia-15α-hydroxy-16,17,18,19,20-pentanor-15-cyclohexyl-, m.p. 158°

6,9-dioxo-11α-tert.-butyldimethylsilyloxy-13-thia-15β-hydroxy-16,17,18,19,20-pentanor-15-cyclohexyl-, m.p. 167°

6,9-dioxo-11α-tert.-butyldimethylsilyloxy-13-thia-15-hydroxy-18,19,20-trinor-17-cyclohexyl-, mixture of isomers, m.p. 156°

6,9-dioxo-11α-tert.-butyldimethylsilyloxy-13-thia-15α-hydroxy-18,19,20-trinor-17-cyclohexyl-, m.p. 149°

6,9-dioxo-11α-tert.-butyldimethylsilyloxy-13-thia-15β-hydroxy-18,19,20-trinor-17-cyclohexyl-, m.p. 160°

6,9-dioxo-11α-tert.-butyldimethylsilyloxy-13-thia-15-hydroxy-16,17,18,19,20-pentanor-15-phenyl-, mixture of isomers, m.p. 146°

6,9-dioxo-11α-tert.-butyldimethylsilyloxy-13-thia-15α-hydroxy-16,17,18,19,20-pentanor-15-phenyl-, m.p. 150°

6,9-dioxo-11α-tert.-butyldimethylsilyloxy-13-thia-15β-hydroxy-16,17,18,19,20-pentanor-15-phenyl-, m.p. 137°

6,9-dioxo-11α-tert.-butyldimethylsilyloxy-13-thia-15-hydroxy-18,19,20-trinor-16-phenyl-, mixture of isomers, m.p. 125°

6,9-dioxo-11α-tert.-butyldimethylsilyloxy-13-thia-15α-hydroxy-18,19,20-trinor-16-phenyl-, m.p. 105°

6,9-dioxo-11α-tert.-butyldimethylsilyloxy-13-thia-15β-hydroxy-18,19,20-trinor-16-phenyl-, m.p. 143°

6,9-dioxo-11α-tert.-butyldimethylsilyloxy-13-thia-15-hydroxy-16-methyl-18,19,20-trinor-17-phenyl-, mixture of isomers 6,9-dioxo-11α-tert.-butyldimethylsilyloxy-13-thia-15α-hydroxy-16-methyl-18,19,20-trinor-17-phenyl- 6,9-dioxo-11α-tert.-butyldimethylsilyloxy-13-thia-15β-hydroxy-16-methyl-18,19,20-trinor-17-phenyl- 6,9-dioxo-11α-tert.-butyldimethylsilyloxy-13-thia-15-hydroxy-16,16-dimethyl-18,19,20-trinor-17-phenyl-, mixture of isomers 6,9-dioxo-11α-tert.-butyldimethylsilyloxy-13-thia-15α-hydroxy-16,16-dimethyl-18,19,20-trinor-17-phenyl- 6,9-dioxo-11α-tert.-butyldimethylsilyloxy-13-thia-15β-hydroxy-16,16-dimethyl-18,19,20-trinor-17-phenyl- 6,9-dioxo-11α-tert.-butyldimethylsilyloxy-13-thia-15-hydroxy-16,17,18,19,20-pentanor-15-p-fluorophenyl-, mixture of isomers 6,9-dioxo-11α-tert.-butyldimethylsilyloxy-13-thia-15α-hydroxy-16,17,18,19,20-pentanor-15-p-fluorophenyl- 6,9-dioxo-11α-tert.-butyldimethylsilyloxy-13-thia-15β-hydroxy-16,17,18,19,20-pentanor-15-p-fluorophenyl- 6,9-dioxo-11α-tert.-butyldimethylsilyloxy-13-thia-15-hydroxy-16,17,18,19,20-pentanor-15-o-chlorophenyl-, mixture of isomers, m.p. 148°

6,9-dioxo-11α-tert.-butyldimethylsilyloxy-13-thia-15α-hydroxy-16,17,18,19,20-pentanor-15-o-chlorophenyl-, m.p. 165°

6,9-dioxo-11α-tert.-butyldimethylsilyloxy-13-thia-15β-hydroxy-16,17,18,19,20-pentanor-15-o-chlorophenyl-, m.p. 137°

6,9-dioxo-11α-tert.-butyldimethylsilyloxy-13-thia-15-hydroxy-16,17,18,19,20-pentanor-15-m-chlorophenyl-, mixture of isomers, m.p. 145°

6,9-dioxo-11α-tert.-butyldimethylsilyloxy-13-thia-15α-hydroxy-16,17,18,19,20-pentanor-15-m-chlorophenyl-, m.p. 150°

6,9-dioxo-11α-tert.-butyldimethylsilyloxy-13-thia-15β-hydroxy-16,17,18,19,20-pentanor-15-m-chlorophenyl-, m.p. 133°

6,9-dioxo-11α-tert.-butyldimethylsilyloxy-13-thia-15-hydroxy-16,17,18,19,20-pentanor-15-p-chlorophenyl-, mixture of isomers, m.p. 139°

6,9-dioxo-11α-tert.-butyldimethylsilyloxy-13-thia-15α-hydroxy-16,17,18,19,20-pentanor-15-p-chlorophenyl- m.p. 143°

6,9-dioxo-11α-tert.-butyldimethylsilyloxy-13-thia-15β-hydroxy-16,17,18,19,20-pentanor-15-p-chlorophenyl-, m.p. 133°

6,9-dioxo-11α-tert.-butyldimethylsilyloxy-13-thia-15-hydroxy-16,17,18,19,20-pentanor-15-p-bromophenyl-, mixture of isomers 6,9-dioxo-11α-tert.-butyldimethylsilyloxy-13-thia-15α-hydroxy-16,17,18,19,20-pentanor-15-p-bromophenyl- 6,9-dioxo-11α-tert.-butyldimethylsilyloxy-13-thia-15β-hydroxy-16,17,18,19,20-pentanor-15-p-bromophenyl- 6,9-dioxo-11α-tert.-butyldimethylsilyloxy-13-thia-15-hydroxy-16,17,18,19,20-pentanor-15-p-tolyl, mixture of isomers 6,9-dioxo-11α-tert.-butyldimethylsilyloxy-13-thia-15α-hydroxy-16,17,18,19,20-pentanor-15-p-tolyl- 6,9-dioxo-11α-tert.-butyldimethylsilyloxy-13-thia-15β-hydroxy-16,17,18,19,20-pentanor-15-p-tolyl- 6,9-dioxo-11α-tert.-butyldimethylsilyloxy-13-thia-15-hydroxy-16,17,18,19,20-pentanor-15-o-methoxyphenyl-, mixture of isomers, m.p. 122°

6,9-dioxo-11α-tert.-butyldimethylsilyloxy-13-thia-15α-hydroxy-16,17,18,19,20-pentanor-15-o-methoxyphenyl-, m.p. 135°

6,9-dioxo-11α-tert.-butyldimethylsilyloxy-13-thia-15β-hydroxy-16,17,18,19,20-pentanor-15-o-methoxyphenyl-, m.p. 103°

6,9-dioxo-11α-tert.-butyldimethylsilyloxy-13-thia-15-hydroxy-16,17,18,19,20-pentanor-15-(2-pyridyl)-, mixture of isomers, m.p. 117°

6,9-dioxo-11α-tert.-butyldimethylsilyloxy-13-thia-15α-hydroxy-16,17,18,19,20-pentanor-15-(2-pyridyl)-

6,9-dioxo-11α-tert.-butyldimethylsilyloxy-13-thia-15β-hydroxy-16,17,18,19,20-pentanor-15-(2-pyridyl)- and p-benzamidophenyl 6,9-dioxo-11α-tert.-butyldimethylsilyloxy-13-thia-15-hydroxy-16-methyl-18-prostinoate, mixture of isomers, m.p. 120°–121°, p-benzamidophenyl ester of 6-oxo-11-O-tert.-butyldimethylsilyl-13-thia-13,14-dihydro-16,17,18,19,20-pentanor-15-phenyl-PGE$_1$, m.p. 126°, p-benzamidophenyl ester of (8,11,12-ent)-6-oxo-11-O-tert.-butyldimethylsilyl-13-thia-13,14-dihydro-16,17,18,19,20-pentanor-15-phenyl-PGE$_1$, m.p. 132°.

EXAMPLE 2

In analogy to Example 1, from 2-hydroxy-3-m-chlorophenoxypropanethiol and p-benzamidophenyl 6-oxo-7-(3-hydroxy-5-oxo-1-cyclopentenyl)heptanoate is obtained p-benzamidophenyl 6,9-dioxo-11α,15-dihydroxy-13-thia-17,18,19,20-tetranor-16-m-chlorophenoxyprostanoate, m.p. 77°.

The following are obtainable in analogy:

p-benzamidophenyl 6,9-dioxo-11α,15-dihydroxy-13-thia-16,17,18,19,20-pentanor-15-o-chlorophenylprostanoate, mixture of isomers p-benzamidophenyl 6,9-dioxo-11α,15α-dihydroxy-13-thia-16,17,18,19,20-pentanor-15-o-chlorophenylprostanoate, m.p. 62° p-benzamidophenyl 6,9-dioxo-11α,15β-dihydroxy-13-thia-16,17,18,19,20-pentanor-15-o-chlorophenylprostanoate, Rf 0.20.

EXAMPLE 3

In analogy to Example 1, from 2-hydroxy-2-methylheptanethiol and p-benzamidophenyl 6-oxo-7-(3-tert.-butoxy-5-oxo-1-cyclopentenyl)heptanoate is obtained p-benzamidophenyl 6,9-dioxo-11α-tert.-butoxy-13-thia-15-hydroxy-15-methylprostanoate as a mixture of isomers.

The following p-benzamidophenyl prostanoates are obtained analogously:

6,9-dioxo-11α-tert.-butoxy-13-thia-15-hydroxy-, mixture of isomers 6,9-dioxo-11α-tert.-butoxy-13-thia-15α-hydroxy- 6,9-dioxo-11α-tert.-butoxy-13-thia-15β-hydroxy- 6,9-dioxo-11α-tert.-butoxy-13-thia-15-hydroxy-20-methyl-, mixture of isomers 6,9-dioxo-11α-tert.-butoxy-13-thia-15α-hydroxy-20-methyl- 6,9-dioxo-11α-tert.-butoxy-13-thia-15β-hydroxy-20-methyl- 6,9-dioxo-11α-tert.-butoxy-13-thia-15-hydroxy-16-methyl-, mixture of isomers 6,9-dioxo-11α-tert.-butoxy-13-thia-15α-hydroxy-16-methyl- 6,9-dioxo-11α-tert.-butoxy-13-thia-15β-hydroxy-16-methyl- 6,9-dioxo-11α-tert.-butoxy-13-thia-15-hydroxy-16,20-dimethyl-, mixture of isomers 6,9-dioxo-11α-tert.-butoxy-13-thia-15α-hydroxy-16,20-dimethyl- 6,9-dioxo-11α-tert.-butoxy-13-thia-15β-hydroxy-16,20-dimethyl- 6,9-dioxo-11α-tert.-butoxy-13-thia-15-hydroxy-17,18,19,20-tetranor-16-m-chlorophenoxy-, mixture of isomers 6,9-dioxo-11α-tert.-butoxy-13-thia-15-hydroxy-16,17,18,19,20-pentanor-15-phenyl-, mixture of isomers 6,9-dioxo-11α-tert.-butoxy-13-thia-15α-hydroxy-16,17,18,19,20-pentanor-15-phenyl- 6,9-dioxo-11α-tert.-butoxy-13-thia-15β-hydroxy-16,17,18,19,20-pentanor-15-phenyl 6,9-dioxo-11α-tert.-butoxy-13-thia-15-hydroxy-16,17,18,19,20-pentanor-15-o-chlorophenyl-, mixture of isomers 6,9-dioxo-11α-tert.-butoxy-13-thia-15α-hydroxy-16,17,18,19,20-pentanor-15-o-chlorophenyl- 6,9-dioxo-11α-tert.-butoxy-13-thia-15β-hydroxy-16,17,18,19,20-pentanor-15-o-chlorophenyl- and p-benzamidophenyl 6,9-dioxo-11α-tert.-butoxy-13-thia-15-hydroxy-16-methyl-18-prostinoate, mixture of isomers p-benzamidophenyl ester of 6-oxo-11-O-tert.-butyl-13-thia-13,14-dihydro-16,17,18,19,20-pentanor-15-phenyl-PGE$_1$ p-benzamidophenyl ester of (8,11,12-ent)-6-oxo-11-O-tert.-butyl-13-thia-13,14-dihydro-16,17,18,19,20-pentanor-15-phenyl-PGE$_1$.

EXAMPLE 4

In analogy to Example 1, from 2-hydroxy-2-methylheptanethiol and p-benzamidophenyl 6-oxo-7-(3-tert.-butoxymethoxy-5-oxo-1-cyclopentenyl)heptanoate is obtained p-benzamidophenyl 6,9-dioxo-11α-tert.-butoxymethoxy-13-thia-15-hydroxy-15-methylprostanoate as a mixture of isomers.

The following p-benzamidophenyl prostanoates are obtained analogously:

6,9-dioxo-11α-tert.-butoxymethoxy-13-thia-15-hydroxy-, mixture of isomers 6,9-dioxo-11α-tert.-butoxymethoxy-13-thia-15α-hydroxy- 6,9-dioxo-11α-tert.-butoxymethoxy-13-thia-15β-hydroxy- 6,9-dioxo-11α-tert.-butoxymethoxy-13-thia-15-hydroxy-20-methyl-, mixture of isomers 6,9-dioxo-11α-tert.-butoxymethoxy-13-thia-15α-hydroxy-20-methyl- 6,9-dioxo-11α-tert.-butoxymethoxy-13-thia-15β-hydroxy-20-methyl- 6,9-dioxo-11α-tert.-butoxymethoxy-13-thia-15-hydroxy-16-methyl-, mixture of isomers 6,9-dioxo-11α-tert.-butoxymethoxy-13-thia-15α-hydroxy-16-methyl- 6,9-dioxo-11α-tert.-butoxymethoxy-13-thia-15β-hydroxy-16-methyl- 6,9-dioxo-11α-tert.-butoxymethoxy-13-thia-15-hydroxy-16,20-dimethyl-, mixture of isomers 6,9-dioxo-11α-tert.-butoxymethoxy-13-thia-15α-hydroxy-16,20-dimethyl- 6,9-dioxo-11α-tert.-butoxymethoxy-13-thia-15β-hydroxy-16,20-dimethyl- 6,9-dioxo-11α-tert.-butoxymethoxy-13-thia-15-hydroxy-17,18,19,20-tetranor-16-m-chlorophenoxy-, mixture of isomers 6,9-dioxo-11α-tert.-butoxymethoxy-13-thia-15-hydroxy-16,17,18,19,20-pentanor-15-phenyl-, mixture of isomers 6,9-dioxo-11α-tert.-butoxymethoxy-13-thia-15α-hydroxy-16,17,18,19,20-pentanor-15-phenyl- 6,9-dioxo-11α-tert.-butoxymethoxy-13-thia-15β-hydroxy-16,17,18,19,20-pentanor-15-phenyl-, 6,9-dioxo-11α-tert.-butoxymethoxy-13-thia-15-hydroxy-16-17,18,19,20-pentanor-15-o-chlorophenyl-, mixture of isomers 6,9-dioxo-11α-tert.-butoxymethoxy-13-thia-15α-hydroxy-16,17,18,19,20-pentanor-15-o-chlorophenyl- 6,9-dioxo-11α-tert.-butoxymethoxy-13-thia-15β-hydroxy-16,17,18,19,20-pentanor-15-o-chlorophenyl- and p-benzamidophenyl 6,9-dioxo-11α-tert.-butoxymethoxy-13-thia-15-hydroxy-16-methyl-18-prostinoate, mixture of isomers p-benzamidophenyl ester of 6-oxo-11-O-tert.-butoxymethyl-13-thia-13,14-dihydro-16,17,18,19,20-pentanor-15-phenyl-PGE$_1$, p-benzamidophenyl ester of (8,11,12-ent)-6-oxo-11-O-tert.-butoxymethyl-13-thia-13,14-dihydroxy-16,17,18,19,20-pentanor-15-phenyl-PGE$_1$.

EXAMPLE 5

In analogy to Example 1, from 2-hydroxy-2-methylheptanethiol and p-benzamidophenyl 6-oxo-7-[3-(tetrahydro-2-pyranyloxy)-5-oxo-1-cyclopentenyl]heptanoate is obtained p-benzamidophenyl 6,9-dioxo-11α-(tetrahydro-2-pyranyloxy)-13-thia-15-hydroxy-15-methylprostanoate as a mixture of isomers.

The following p-benzamidophenyl prostanoates are obtained analogously:

6,9-dioxo-11α-(tetrahydro-2-pyranyloxy)-13-thia-15-hydroxy- mixture of isomers
6,9-dioxo-11α-(tetrahydro-2-pyranyloxy)-13-thia-15α-hydroxy-
6,9-dioxo-11α-(tetrahydro-2-pyranyloxy)-13-thia-15β-hydroxy-
6,9-dioxo-11α-(tetrahydro-2-pyranyloxy)-13-thia-15-hydroxy-20-methyl-, mixture of isomers
6,9-dioxo-11α-(tetrahydro-2-pyranyloxy)-13-thia-15α-hydroxy-20-methyl-
6,9-dioxo-11α-(tetrahydro-2-pyranyloxy)-13-thia-15βhydroxy-20-methyl-
6,9-dioxo-11α-(tetrahydro-2-pyranyloxy)-13-thia-15-hydroxy-16-methyl-, mixture of isomers
6,9-dioxo-11α-(tetrahydro-2-pyranyloxy)-13-thia-15α-hydroxy-16-methyl-
6,9-dioxo-11α-(tetrahydro-2-pyranyloxy)-13-thia-15β-hydroxy-16-methyl-
6,9-dioxo-11α-(tetrahydro-2-pyranyloxy)-13-thia-15-hydroxy-16,20-dimethyl-, mixture of isomers
6,9-dioxo-11α-(tetrahydro-2-pyranyloxy)-13-thia-15α-hydroxy-16,20-dimethyl-
6,9-dioxo-11α-(tetrahydro-2-pyranyloxy)-13-thia-15β-hydroxy-16,20-dimethyl-
6,9-dioxo-11α-(tetrahydro-2-pyranyloxy)-13-thia-15-hydroxy-17,18,19,20-tetranor-16-m-chlorophenoxy-, mixture of isomers
6,9-dioxo-11α-(tetrahydro-2-pyranyloxy)-13-thia-15-hydroxy-16,17,18,19,20-pentanor-15-phenyl, mixture of isomers,
6,9-dioxo-11α-(tetrahydro-2-pyranyloxy)-13-thia-15α-hydroxy-16,17,18,19,20-pentanor-15-phenyl-
6,9-dioxo-11α-(tetrahydro-2-pyranyloxy)-13-thia-15β-hydroxy-16,17,18,19,20-pentanor-15-phenyl-
6,9-dioxo-11α-(tetrahydro-2-pyranyloxy)-13-thia-15-hydroxy-16,17,18,19,20-pentanor-15-o-chlorophenyl, mixture of isomers
6,9-dioxo-11α-(tetrahydro-2-pyranyloxy)-13-thia-15α-hydroxy-16,17,18,19,20-pentanor-15-o-chlorophenyl-
6,9-dioxo-11α-(tetrahydro-2-pyranyloxy)-13-thia-15β-hydroxy-16,17,18,19,20-pentanor-15-o-chlorophenyl- and
p-benzamidophenyl 6,9-dioxo-11α-(tetrahydro-2-pyranyloxy)-13-thia-15-hydroxy-16-methyl-18-prostinoate, mixture of isomers
p-benzamidophenyl ester of 6-oxo-11-O-(tetrahydro-2-pyranyl)-13-thia-13,14-dihydro-16,17,18,19,20-pentanor-15-phenyl-PGE$_1$
p-benzamidophenyl ester of (8,11,12-ent)-6-oxo-11-O-(tetrahydro-2-pyranyl)-13-thia-13,14-dihydro-16,17,18,19,20-pentanor-15-phenyl-PGE$_1$.

EXAMPLE 6

In analogy to Example 1, from 2-hydroxy-2-methylheptanethiol and p-benzamidophenyl 6-oxo-7-(3-acetoxy-5-oxo-1-cyclopentenyl)heptanoate is obtained p-benzamidophenyl 6,9-dioxo-11α-acetoxy-13-thia-15-hydroxy-15-methylprostanoate as a mixture of isomers.

The following p-benzamidophenyl prostanoates are obtained analogously:

6,9-dioxy-11α-acetoxy-13-thia-15-hydroxy-, mixture of isomers
6,9-dioxy-11α-acetoxy-13-thia-15α-hydroxy-
6,9-dioxy-11α-acetoxy-13-thia-15β-hydroxy-
6,9-dioxy-11α-acetoxy-13-thia-15-hydroxy-20-methyl-, mixture of isomers
6,9-dioxy-11α-acetoxy-13-thia-15α-hydroxy-20-methyl-
6,9-dioxy-11α-acetoxy-13-thia-15β-hydroxy-20-methyl-
6,9-dioxy-11α-acetoxy-13-thia-15-hydroxy-16-methyl-, mixture of isomers
6,9-dioxy-11α-acetoxy-13-thia-15α-hydroxy-16-methyl-
6,9-dioxy-11α-acetoxy-13-thia-15β-hydroxy-16-methyl-
6,9-dioxy-11α-acetoxy-13-thia-15-hydroxy-16,20-dimethyl-, mixture of isomers
6,9-dioxy-11α-acetoxy-13-thia-15α-hydroxy-16,20-dimethyl-
6,9-dioxy-11α-acetoxy-13-thia-15β-hydroxy-16,20-dimethyl-
6,9-dioxy-11α-acetoxy-13-thia-15-hydroxy-17,18,19,20-tetranor-16-m-chlorophenoxy-, mixture of isomers
6,9-dioxo-11α-acetoxy-13-thia-15-hydroxy-16,17,18,19,20-pentanor-15-phenyl-, mixture of isomers
6,9-dioxo-11α-acetoxy-13-thia-15α-hydroxy-16,17,18,19,20-pentanor-15-phenyl-
6,9-dioxo-11α-acetoxy-13-thia-15β-hydroxy-16,17,18,19,20-pentanor-15-phenyl-
6,9-dioxo-11α-acetoxy-13-thia-15-hydroxy-16,17,18,19,20-pentanor-15-o-chlorophenyl-, mixture of isomers
6,9-dioxy-11α-acetoxy-13-thia-15α-hydroxy-16,17,18,19,20-pentanor-15-chlorophenyl-
6,9-dioxy-11α-acetoxy-13-thia-15β-hydroxy-16,17,18,19,20-pentanor-15-o-chlorophenyl- and
p-benzamidophenyl 6,9-dioxy-11α-acetoxy-13-thia-15-hydroxy-16-methyl-18-prostinoate, mixture of isomers
p-benzamidophenyl ester of 6-oxo-11-O-acetyl-13-thia-13,14-dihydro-16,17,18,19,20-pentanor-15-phenyl-PGE$_1$,
p-benzamidophenyl ester of (8,11,12-ent)-6-oxo-11-O-acetyl-13-thia-13,14-dihydro-16,17,18,19,20-pentanor-15-phenyl-PGE$_1$.

EXAMPLE 7

In analogy to Example 1, from 2-hydroxy-2-methylheptanethiol and p-benzamidophenyl 6-oxo-7-(3-trimethylacetoxy-5-oxo-1-cyclopentenyl)heptanoate is obtained p-benzamidophenyl 6,9-dioxo-11α-trimethylacetoxy-13-thia-15-hydroxy-15-methylprostanoate as a mixture of isomers.

The following p-benzamidophenyl prostanoates are obtained analogously:

6,9-dioxo-11α-trimethylacetoxy-13-thia-15-hydroxy-, mixture of isomers
6,9-dioxo-11α-trimethylacetoxy-13-thia-15α-hydroxy-
6,9-dioxo-11α-trimethylacetoxy-13-thia-15β-hydroxy-
6,9-dioxo-11α-trimethylacetoxy-13-thia-15-hydroxy-20-methyl-, mixture of isomers
6,9-dioxo-11α-trimethylacetoxy-13-thia-15α-hydroxy-20-methyl- 6,9-dioxo-11α-trimethylacetoxy-13-thia-15β-hydroxy-20-methyl-
6,9-dioxo-11α-trimethylacetoxy-13-thia-15-hydroxy-16-methyl-, mixture of isomers
6,9-dioxo-11α-trimethylacetoxy-13-thia-15α-hydroxy-16-methyl-
6,9-dioxo-11α-trimethylacetoxy-13-thia-15β-hydroxy-16-methyl-
6,9-dioxo-11α-trimethylacetoxy-13-thia-15-hydroxy-16,20-dimethyl-, mixture of isomers
6,9-dioxo-11α-trimethylacetoxy-13-thia-15α-hydroxy-16,20-dimethyl-
6,9-dioxo-11α-trimethylacetoxy-13-thia-15β-hydroxy-16,20-dimethyl-
6,9-dioxo-11α-trimethylacetoxy-13-thia-15-hydroxy-17,18,19,20-tetranor-16-m-chlorophenoxy-, mixture of isomers
6,9-dioxo-11α-trimethylacetoxy-13-thia-15-hydroxy-16,17,18,19,20-pentanor-15-phenyl-, mixture of isomers
6,9-dioxo-11α-trimethylacetoxy-13-thia-15α-hydroxy-16,17,18,19,20-pentanor-15-phenyl-
6,9-dioxo-11α-trimethylacetoxy-13-thia-15β-hydroxy-16,17,18,19,20-pentanor-15-phenyl-
6,9-dioxo-11α-trimethylacetoxy-13-thia-16-hydroxy-16,17,18,19,20-pentanor-15-o-chlorophenyl-, mixture of isomers
6,9-dioxo-11α-trimethylacetoxy-13-thia-15α-hydroxy-16,17,18,19,20-pentanor-15-o-chlorophenyl-
6,9-dioxo-11α-trimethylacetoxy-13-thia-15β-hydroxy-16,17,18,19,20-pentanor-15-o-chlorophenyl- and
p-benzamidophenyl 6,9-dioxo-11α-trimethylacetoxy-13-thia-15-hydroxy-16-methyl-18-prostinoate, mixture of isomers,
p-benzamidophenyl ester of 6-oxo-11-O-trimethylacetyl-13-thia-13,14-dihydro-16,17,18,19,20-pentanor-15-phenyl-PGE$_1$,
p-benzamidophenyl ester of (8,11,12-ent)-6-oxo-11-O-trimethylacetyl-13-thia-13,14-dihydro-16,17,18,19,20-pentanor-15-phenyl-PGE$_1$.

EXAMPLE 8

In analogy to Example 1, from 2-hydroxy-2-methylheptanethiol and p-benzamidophenyl 6-oxo-7-(3-tert.-butylacetoxy-5-oxo-1-cyclopentenyl)heptanoate is obtained p-benzamidophenyl 6,9-dioxo-11α-tert.-butylacetoxy-13-thia-15-hydroxy-15-methylprostanoate as a mixture of isomers.

The following p-benzamidophenyl prostanoates are obtained analogously:
6,9-dioxo-11α-tert.-butylacetoxy-13-thia-15-hydroxy-, mixture of isomers
6,9-dioxo-11α-tert.-butylacetoxy-13-thia-15α-hydroxy-
6,9-dioxo-11α-tert.-butylacetoxy-13-thia-15β-hydroxy-
6,9-dioxo-11α-tert.-butylacetoxy-13-thia-15-hydroxy-20-methyl-, mixtures of isomers
6,9-dioxo-11α-tert.-butylacetoxy-13-thia-15α-hydroxy-20-methyl-
6,9-dioxo-11α-tert.-butylacetoxy-13-thia-15β-hydroxy-20-methyl-
6,9-dioxo-11α-tert.-butylacetoxy-13-thia-15-hydroxy-16-methyl-, mixture of isomers
6,9-dioxo-11α-tert.-butylacetoxy-13-thia-15α-hydroxy-16-methyl-
6,9-dioxo-11α-tert.-butylacetoxy-13-thia-15β-hydroxy-16-methyl-
6,9-dioxo-11α-tert.-butylacetoxy-13-thia-15-hydroxy-16,20-dimethyl-, mixture of isomers
6,9-dioxo-11α-tert.-butylacetoxy-13-thia-15α-hydroxy-16,20-dimethyl-
6,9-dioxo-11α-tert.-butylacetoxy-13-thia-15β-hydroxy-16,20-dimethyl-
6,9-dioxo-11α-tert.-butylacetoxy-13-thia-15-hydroxy-17,18,19,20-tetranor-16-m-chlorophenoxy-, mixture of isomers
6,9-dioxo-11α-tert.-butylacetoxy-13-thia-15-hydroxy-16,17,18,19,20-pentanor-15-phenyl-, mixture of isomers
6,9-dioxo-11α-tert.-butylacetoxy-13-thia-15α-hydroxy-16,17,18,19,20-pentanor-15-phenyl-
6,9-dioxo-11α-tert.-butylacetoxy-13-thia-15β-hydroxy-16,17,18,19,20-pentanor-15-phenyl-
6,9-dioxo-11α-tert.-butylacetoxy-13-thia-15-hydroxy-16,17,18,19,20-pentanor-15-o-chlorophenyl-, mixture of isomers
6,9-dioxo-11α-tert.-butylacetoxy-13-thia-15α-hydroxy-16,17,18,19,20-pentanor-15-o-chlorophenyl-
6,9-dioxo-11α-tert.-butylacetoxy-13-thia-15β-hydroxy-16,17,18,19,20-pentanor-15-o-chlorophenyl- and
p-benzamidophenyl 6,9-dioxo-11α-tert.-butylacetoxy-13-thia-15-hydroxy-16-methyl-18-prostinoate, mixture of isomers
p-benzamidophenyl ester of 6-oxo-11-O-tert.-butylacetyl-13-thia-13,14-dihydro-16,17,18,19,20-pentanor-15-phenyl-PGE$_1$,
p-benzamidophenyl ester of (8,11,12-ent)-6-oxo-11-O-tert.-butylacetyl-13-thia-13,14-dihydro-16,17,18,19,20-pentanor-15-phenyl-PGE$_1$.

EXAMPLE 9

A solution of 24 g of 2-hydroxy-2-methylheptanethiol and 84 g of diisopropylamine in 300 ml of THF is boiled for 2 hours, then cooled to =25°, and a precooled solution of 24 g of 6-oxo-7-(3-hydroxy-5-oxo-1-cyclopentenyl)heptanoic acid in 75 ml of THF is added. The process is continued as indicated in Example 1, and 6,9-dioxo-11α,15-dihydroxy-13-thia-15-methylprostanoic acid is obtained as an oil.

The following are obtained analogously:
methyl 6,9-dioxo-11α,15-dihydro-13-thia-15-methylprostanoate
butyl 6,9-dioxo-11α,15-dihydro-13-thia-15-methylprostanoate
phenyl 6,9-dioxo-11α,15-dihydro-13-thia-15-methylprostanoate
p-biphenyl 6,9-dioxo-11α,15-dihydroxy-13-thia-15-methylprostanoate
6,9-dioxo-11α,15-dihydroxy-13-thia-16-methyl-18-prostenoic acid
6,9-dioxo-11α,15-dihydroxy-13-thia-15,16-dimethylprostanoic acid
6,9-dioxo-11α,15-dihydroxy-13-thia-16,16-dimethylprostanoic acid
6,9-dioxo-11α,15-dihydroxy-13-thia-17-phenyl-18,19,20-trinorprostanoic acid
6,9-dioxo-11α,15-dihydroxy-13-thia-20-fluoroprostanoic acid
6,9-dioxo-11α,15-dihydroxy-13-thia-16-cyclopentyl-17,18,19,20-tetranorprostanoic acid
6,9-dioxo-11α,15-dihydroxy-13-thia-16-cyclohexyl-17,18,19,20-tetranorprostanoic acid
6,9-dioxo-11α,15-dihydroxy-13-thia-16-(4-methylcyclohexyl)-17,18,19,20-tetranorprostanoic acid
6,9-dioxo-11α,15-dihydroxy-13-thia-17-p-fluorophenyl-18,19,20-trinorprostanoic acid 6,9-dioxo-11α,15-dihydroxy-13-thia-17-p-bromophenyl-18,19,20-trinorprostanoic acid
6,9-dioxo-11α,15-dihydroxy-13-thia-17-p-tolyl-18,19,20-trinorprostanoic acid
6,9-dioxo-11α,15-dihydroxy-13-thia-17-p-hydroxyphenyl-18,19,20-trinorprostanoic acid
6,9-dioxo-11α,15-dihydroxy-13-thia-17-p-methoxyphenyl-18,19,20-trinorprostanoic acid
6,9-dioxo-11α,15-dihydroxy-13-thia-17-m-trifluoromethylphenyl-18,19,20-trinorprostanoic acid
6,9-dioxo-11α,15-dihydroxy-13-thia-17-(4-pyridyl)-18,19,20-trinorprostanoic acid
6,9-dioxo-11α,15-dihydroxy-13-thia-17-(1-naphthyl)-18,19,20-trinorprostanoic acid
6,9-dioxo-11α,15-dihydroxy-13-thia-17-(2-thienyl)-18,19,20-trinorprostanoic acid
6,9-dioxo-11α,15-dihydroxy-13-thia-17-methoxy-18,19,20-trinorprostanoic acid
6,9-dioxo-11α,15-dihydroxy-13-thia-17-methylthio-18,19,20-trinorprostanoic acid
6,9-dioxo-11α,15-dihydroxy-13-thia-16-phenoxy-18,19,20-trinorprostanoic acid
6,9-dioxo-11α,15-dihydroxy-13-thia-16-p-fluorophenoxy-18,19,20-trinorprostanoic acid
6,9-dioxo-11α,15-dihydroxy-13-thia-16-(3,4,5-trimethoxyphenoxy)-18,19,20-trinorprostanoic acid.

EXAMPLE 10

10 g of p-benzamidophenyl 6,9-dioxo-11α-tert.-butyl-dimethylsilyloxy-13-thia-15-hydroxy-15-methylprostanoate are dissolved in a mixture of 43 ml of 40% hydrofluoric acid and 243 ml of acetonitrile, and the solution is stirred at 20° for 2.5 hours, then NaHCO₃ is added to pH 8, and the mixture is worked up as usual. p-Benzamidophenyl 6,9-dioxo-11α,15-dihydroxy-13-thia-15-methylprostanoate is obtained as a mixture of isomers, m.p. 69°–70°.

The following p-benzamidophenyl prostanoates can be obtained analogously by hydrolysis of the appropriate 3α-tert.-butyldimethylsilyl ethers:
6,9-dioxo-11α,15α-dihydroxy-13-thia-15-methyl-
6,9-dioxo-11α,15β-dihydroxy-13-thia-15-methyl-
6,9-dioxo-11α,15-dihydroxy-13-thia, mixture of isomers
6,9-dioxo-11α,15α-dihydroxy-13-thia-, m.p. 94°
6,9-dioxo-11α,15β-dihydroxy-13-thia-, m.p. 113°
6,9-dioxo-11α,15-dihydroxy-13-thia-20-methyl-, mixture of isomers
6,9-dioxo-11α,15α-dihydroxy-13-thia-20-methyl-, m.p. 93°
6,9-dioxo-11α,15β-dihydroxy-13-thia-20-methyl- m.p. 113°
6,9-dioxo-11α,15-dihydroxy-13-thia-16-methyl-, mixture of isomers
6,9-dioxo-11α,15α-dihydroxy-13-thia-16-methyl-, m.p. 99°
6,9-dioxo-11α,15β-dihydroxy-13-thia-16-methyl-, m.p. 114°
6,9-dioxo-11α,15-dihydroxy-13-thia-16,20-dimethyl-, mixture of isomers, m.p. 76°
6,9-dioxo-11α,15α-dihydroxy-13-thia-16,20-dimethyl-, m.p. 69°–70°
6,9-dioxo-11α,15β-dihydroxy-13-thia-16,20-dimethyl-, m.p. 81°–82°
6,9-dioxo-11α,15-dihydroxy-13-thia-20-ethyl-, mixture of isomers, m.p. 64
6,9-dioxo-11α,15α-dihydroxy-13-thia-20-ethyl-, m.p. 63°
6,9-dioxo-11α,15β-dihydroxy-13-thia-20-ethyl-, m.p. 79°
6,9-dioxo-11α,15-dihydroxy-13-thia-15,20-dimethyl-, mixture of isomers, m.p. 71°
6,9-dioxo-11α,15α-dihydroxy-13-thia-15,20-dimethyl-
6,9-dioxo-11α,15β-dihydroxy-13-thia-15,20-dimethyl-
6,9-dioxo-11α,15-dihydroxy-13-thia-16,16,21-trimethyl-, mixture of isomers
6,9-dioxo-11α,15α-dihydroxy-13-thia-16,16,21-trimethyl-
6,9-dioxo-11α,15β-dihydroxy-13-thia-16,16,21-trimethyl-
6,9-dioxo-11α,15-dihydroxy-13-thia-15-methyl-20-ethyl-, mixture of isomers, m.p. 73°
6,9-dioxo-11α,15α-dihydroxy-13-thia-15-methyl-20-ethyl-
6,9-dioxo-11α,15β-dihydroxy-13-thia-15-methyl-20-ethyl-
6,9-dioxo-11α,15-dihydroxy-13-thia-16-methyl-20-ethyl-, mixture of isomers, Rf 0.49–0.52
6,9-dioxo-11α,15α-dihydroxy-13-thia-16-methyl-20-ethyl-, Rf 0.52
6,9-dioxo-11α,15β-dihydroxy-13-thia-16-methyl-20-ethyl-, m.p. 87°, Rf 0.49
6,9-dioxo-11α,15-dihydroxy-13-thia-16,17,18,19,20-pentanor-15-cyclohexyl-, mixture of isomers, m.p. 83°
6,9-dioxo-11α,15α-dihydroxy-13-thia-16,17,18,19,20-pentanor-15-cyclohexyl-, m.p. 78°
6,9-dioxo-11α,15β-dihydroxy-13-thia-16,17,18,19,20-pentanor-15-cyclohexyl-, m.p. 90°
6,9-dioxo-11α,15-dihydroxy-13-thia-18,19,20-trinor-17-cyclohexyl-, mixture of isomers, Rf 0.45–0.5
6,9-dioxo-11α,15α-dihydroxy-13-thia-18,19,20-trinor-17-cyclohexyl-, Rf 0.5
6,9-dioxo-11α,15β-dihydroxy-13-thia-18,19,20-trinor-17-cyclohexyl-, Rf 0.45
6,9-dioxo-11α,15-dihydroxy-13-thia-16,17,18,19,20-pentanor-15-phenyl, mixture of isomers, Rf 0.40–0.45
6,9-dioxo-11α,15α-dihydroxy-13-thia-16,17,18,19,20-pentanor-15-phenyl-, Rf 0.45
6,9-dioxo-11α,15β-dihydroxy-13-thia-16,17,18,19,20-pentanor-15-phenyl-, m.p. 125°, Rf 0.40
6,9-dioxo-11α,15-dihydroxy-13-thia-18,19,20-trinor-16-phenyl-, mixture of isomers, Rf 0.40–0.45
6,9-dioxo-11α,15α-dihydroxy-13-thia-18,19,20-trinor-16-phenyl-, Rf 0.45
6,9-dioxo-11α,15β-dihydroxy-13-thia-18,19,20-trinor-16-phenyl-, Rf 0.40
6,9-dioxo-11α,15-dihydroxy-13-thia-16-methyl-18,19,20-trinor-17-phenyl-, mixture of isomers, Rf 0.3–0.4
6,9-dioxo-11α,15α-dihydroxy-13-thia-16-methyl-18,19,20-trinor-17-phenyl-, m.p. 130°, Rf 0.4
6,9-dioxo-11α,15β-dihydroxy-13-thia-16-methyl-18,19,20-trinor-17-phenyl-, Rf 0.3
6,9-dioxo-11α,15-dihydroxy-13-thia-16,16-dimethyl-18,19,20-trinor-17-phenyl-
6,9-dioxo-11α,15α-dihydroxy-13-thia-16,16-dimethyl-18,19,20-trinor-17-phenyl-
6,9-dioxo-11α,15β-dihydroxy-13-thia-16,16-dimethyl-18,19,20-trinor-17-phenyl-
6,9-dioxo-11α,15-dihydroxy-13-thia-16,17,18,19,20-pentanor-15-p-fluorophenyl-, mixture of isomers, Rf 0.42–0.45
6,9-dioxo-11α,15α-dihydroxy-13-thia-16,17,18,19,20-pentanor-15-p-fluorophenyl-, Rf 0.45
6,9-dioxo-11α,15β-dihydroxy-13-thia-16,17,18,19,20-pentanor-15-p-fluorophenyl-, Rf 0.42

6,9-dioxo-11α,15-dihydroxy-13-thia-16,17,18,19,20-pentanor-15-o-chlorophenyl-, mixture of isomers, Rf 0.08–0.12 (CH$_2$Cl$_2$/CH$_3$OH 97:3)
6,9-dioxo-11α,15α-dihydroxy-13-thia-16,17,18,19,20-pentanor-15-o-chlorophenyl-, m.p. 62°, Rf 0.12
6,9-dioxo-11α,15β-dihydroxy-13-thia-16,17,18,19,20-pentanor-15-o-chlorophenyl-, Rf 0.08 (CH$_2$Cl$_2$/CH$_3$OH 97:3)
6,9-dioxo-11α,15-dihydroxy-13-thia-16,17,18,19,20-pentanor-15-m-chlorophenyl-, mixture of isomers, Rf 0.5–0.55 (toluene/acetone 3:2)
6,9-dioxo-11α,15α-dihydroxy-13-thia-16,17,18,19,20-pentanor-15-m-chloropheny-, m.p. 113°, Rf 0.55 (toluene/acetone 3:2)
6,9-dioxo-11α,15β-dihydroxy-13-thia-16,17,18,19,20-pentanor-15-m-chlorophenyl-, Rf 0.5 (toluene/acetone 3:2)
6,9-dioxo-11α,15-dihydroxy-13-thia-16,17,18,19,20-pentanor-15-p-chlorophenyl-, mixture of isomers
6,9-dioxo-11α,15α-dihydroxy-13-thia-16,17,18,19,20-pentanor-15-p-chlorophenyl-, m.p. 18°
6,9-dioxo-11α,15β-dihydroxy-13-thia-16,17,18,19,20-pentanor-15-p-chloropehnyl-, m.p. 18°
6,9-dioxo-11α,15-dihydroxy-13-thia-16,17,18,19,20-pentanor-15-p-bromophenyl-, mixture of isomers, Rf 0.42–0.47
6,9-dioxo-11α,15α-dihydroxy-13-thia-16,17,18,19,20-pentanor-15-p-bromophenyl-, Rf 0.47
6,9-dioxo-11α,15β-dihydroxy-13-thia-16,17,18,19,20-pentanor-15-p-bromophenyl-, m.p. 142° Rf, 0.42
6,9-dioxo-11α,15-dihydroxy-13-thia-16,17,18,19,20-pentanor-15-p-tolyl-, mixture of isomers
6,9-dioxo-11α,15α-dihydroxy-13-thia-16,17,18,19,20-pentanor-15-p-tolyl-, m.p. 94°
6,9-dioxo-11α,15β-dihydroxy-13-thia-16,17,18,19,20-pentanor-15-p-tolyl-, m.p. 89°
6,9-dioxo-11α,15-dihydroxy-13-thia-16,17,18,19,20-pentanor-15-o-methoxyphenyl-, mixture of isomers, m.p. 83°
6,9-dioxo-11α,15α-dihydroxy-13-thia-16,17,18,19,20-pentanor-15-o-methoxyphenyl-, m.p. 85°
6,9-dioxo-11α,15β-dihydroxy-13-thia-16,17,18,19,20-pentanor-15-o-methoxyphenyl-, m,p. 85°
6,9-dioxo-11α,15-dihydroxy-13-thia-16,17,18,19,20-pentanor-15-(2-pyridyl)-, mixture of isomers, Rf 0.2 (CH$_2$Cl$_2$/CH$_3$OH 94:6)
6,9-dioxo-11α,15α-dihydroxy-13-thia-16,17,18,19,20-pentanor-15-(2-pyridyl)-
6,9-dioxo-11α,15β-dihydroxy-13-thia-16,17,18,19,20-pentanor-15-(2-pyridyl)- and
p-benzamidophenyl 6,9-dioxo-11α,15-dihydroxy-13-thia-16-methyl-18-prostinoate, mixture of isomers
p-benzamidophenyl ester of 6-oxo-13-thia-13,14-dihydro-16,17,18,19,20-pentanor-15-phenyl-PGE$_1$
p-benzamidophenyl ester of (8,11,12-ent)-6-oxo-13-thia-13,14-dihydro-16,17,18,19,20-pentanor-15-phenyl-PGE$_1$.

EXAMPLE 11

1 g of p-benzamidophenyl 6,9-dioxo-11α,15-dihydroxy-13-thia-15-methylprostanoate and 1 ml of pancreatic lipase (E. Merck) in 100 ml of water are stirred at 20° for 24 hours, and the mixture is chromatographed on RP silica gel using acetonitrile/water 1:1, and 6,9-dioxo-11α,15-dihydroxy-13-thia-15-methylprostanoic acid is obtained as an oil.

The following are obtained analogously by enzymatic hydrolysis of the appropriate p-benzamidophenyl esters:
6,9-dioxo-11α,15-dihydroxy-13-thiaprostanoic acid, mixture of isomers
6,9-dioxo-11α,15α-dihydroxy-13-thiaprostanoic acid
6,9-dioxo-11α,15β-dihydroxy-13-thiaprostanoic acid
6,9-dioxo-11α,15-dihydroxy-13-thia-20-methylprostanoic acid, mixture of isomers
6,9-dioxo-11α,15α-dihydroxy-13-thia-20-methylprostanoic acid
6,9-dioxo-11α,15β-dihydroxy-13-thia-20-methylprostanoic acid
6,9-dioxo-11α,15-dihydroxy-13-thia-16-methylprostanoic acid, mixture of isomers
6,9-dioxo-11α,15α-dihydroxy-13-thia-16-methylprostanoic acid
6,9-dioxo-11α,15β-dihydroxy-13-thia-16-methylprostanoic acid
6,9-dioxo-11α,15-dihydroxy-13-thia-16,20-dimethylprostanoic acid, mixture of isomers
6,9-dioxo-11α,15α-dihydroxy-13-thia-16,20-dimethylprostanoic acid
6,9-dioxo-11α,15β-dihydroxy-13-thia-16,20-dimethylprostanoic acid
6,9-dioxo-11α,15-dihydroxy-13-thia-17,18,19,20-tetranor-16-m-chlorophenoxyprostanoic acid, mixture of isomers
6,9-dioxo-11α,15α-dihydroxy-13-thia-17,18,19,20-tetranor-16-m-chlorophenoxyprostanoic acid
6,9-dioxo-11α,15β-dihydroxy-13-thia-17,18,19,20-tetranor-16-m-chlorophenoxyprostanoic acid
6,9-dioxo-11α,15-dihydroxy-13-thia-16,17,18,19,20-pentanor-15-o-chlorophenylprostanoic acid, mixture of isomers
6,9-dioxo-11α,15α-dihydroxy-13-thia-16,17,18,19,20-pentanor-15-o-chlorophenylprostanoic acid
6,9-dioxo-11α,15β-dihydroxy-13-thia-16,17,18,19,20-pentanor-15-o-chlorophenylprostanoic acid and
6,9-dioxo-11α,15-dihydroxy-13-thia-16-methyl-18-prostinoic acid
6-oxo-13-thia-13,14-dihydro-16,17,18,19,20-pentanor-15-phenyl-PGE$_1$
(8,11,12-ent)-6-oxo-13-thia-13,14-dihydro-16,17,18,19,20-pentanor-15-phenyl-PGE$_1$.

EXAMPLE 12

A mixture of 5.85 g of p-benzamidophenyl 6,9-dioxo-11α,15-dihydroxy-13-thia-15-methylprostanoate, 2.3 g of tert.-butyldimethylchlorosilane, 2.1 g of imidazole and 300 ml of DMF is stirred at 20° for 16 hours and is worked up as usual. p-Benzamidophenyl 6,9-dioxo-11α-tert.-butyldimethylsilyloxy-13-thia-15-hydroxy-15-methylprostanoate is obtained as a mixture of isomers, m.p. 112°.

EXAMPLE 13

A mixture of 1 g of methyl 6,9-dioxo-11α,15-dihydroxy-13-thia-15-methylprostanoate, 15 ml of acetic anhydride and 2 drops of pyridine is stirred at 20° for 16 hours and is worked up as usual. Methyl 6,9-dioxo-11α-acetoxy-13-thia-15-hydroxy-15-methylprostanoate is obtained as a mixture of isomers.

EXAMPLE 14

50 ml of 0.1N sodium hydroxide solution are added to a solution of 2.09 g of 6,9-dioxo-11α,15-dihydroxy-13- thia-16,20-dimethylprostanoic acid in 30 ml of absolute methanol and the solution is immediately freeze-dried. The sodium salt of 6,9-dioxo-11α,15-dihydroxy-13-thia-16,20-dimethylprostanoic acid is obtained.

The examples which follow relate to mixtures of compounds of the formula I with vehicles or auxiliaries customary in pharmacy, which can be used, in particular, are medicaments:

EXAMPLE A:

Tablets

A mixture comprising 3 g of p-benzamidophenyl 6,9-dioxo-11α-tert.-butyldimethylsilyloxy-13-thia-15-hydroxy-15-methylprostanoate, 50 g of lactose, 16 g of maize starch, 2 g of cellulose powder and 2 g of magnesium stearate is compressed in the usual manner to produce tablets such that each tablet contains 1 mg of the active compound.

EXAMPLE B

Coated tablets

Tablets are formed by compression in analogy to Example A, and these are then coated in a usual manner with a coating which is composed of sugar, maize starch, talc and tragacanth.

EXAMPLE C

Solutions for injection 0.1 g of p-benzamidophenyl 6,9-dioxo-11α,15-dihydroxy-13-thia-15-methylprosanoate is dissolved in 5 ml of ethanol, the solution is diluted with 0.5 l of water and is sterilized by filtration. The resulting solution for injection is dispensed as required into ampoules containing 2.5 ml, 5 ml or 10 ml of the solution for injection. Each ampoule contains 0.05, 0.1 or 0.2 mg of active compound.

Tablets, coated tablets and solutions for injection which contain one or more of the other active compounds of the formula I can be obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A sulphur-containing 6-ketoprostaglandin of the formula

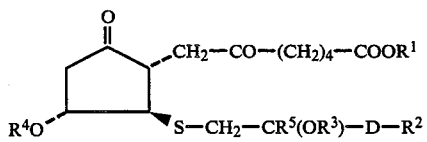

in which
D is a bond, alkylene of 1-3 C atoms, cis-alkenylene of 2-5 C atoms or alkinylene of 2-5 C atoms,
$R^1$ is H, alkyl or 1-4 C atoms, aryl of 6-12 C atoms or —$C_6H_4NHCOC_6H_5$,
$R^2$ is alkyl of 1-7 C atoms, alkyl of 1-7 C atoms substituted by halogen, cycloalkyl of 5-6 C atoms, cycloalkyl of 5-6 C atoms substituted by alkyl of 1-4 C atoms, phenyl, phenyl substituted by F, Cl, Br, alkyl of 1-4 C atoms, OH, $OCH_3$ or $CF_3$, pyridyl, naphthyl, or thienyl, and when D is alkylene of 1-3 C atoms, $R_2$ also can be alkoxy of 1-4 C atoms, alkylthio of 1-4 C atoms, phenoxy or phenoxy substituted by F, Cl, Br, alkyl of 1-4 C atoms, OH, $OCH_3$ or $CF_3$,
$R^3$ and $R^4$ each are H, alkyl of 1-7 C atoms, tetrahydro-2-pyranyl, trialkylsilyl of a total of 3-12 C atoms, aryldialkylsilyl of a total of 8-18 C atoms, alkoxymethyl of 2-5 C atoms, aryloxymethyl of 7-11 C atoms, alkanoyl of 1-10 C atoms, aroyl of 7-10 C atoms, $C_{1-7}$-alkoxycarbonyl or $C_{7-11}$-aralkoxycarbonyl, and
$R^5$ is H or alkyl of 1-3 C atoms,
... indicates that this bond is α,
—— indicates that this bond is β, or, when $R^1$ is H, a physiologically acceptable salt thereof.

2. p-Benzamidophenyl 6,9-dioxo-11α-tert-butyldimethysilyloxy-13-thia-16,20-dimethylprostanoate, a compound of claim 1.

3. p-Benzamidophenyl 6,9-dioxo-11α-tert-butyldimethylsilyloxy-13-thia-15-hydroxy-15-methylprostanoate, a compound of claim 1.

4. p-Benzamidophenyl 6,9-dioxo-11α,15-dihydroxy-13-thia-15-methylprostanoate, a compound of claim 1.

5. A compound of claim 1, wherein D is a bond or —$CH_2$—.

6. A compound of claim 1, wherein $R^1$ is H, methyl, ethyl or —$C_6H_4$—NH—CO—$C_6H_5$.

7. A compound of claim 1, wherein $R^2$ is alkyl of 1-6 C atoms, cyclohexyl, phenyl, phenyl substituted by F, Cl, $CH_3$, $OCH_3$ or $CF_3$, or naphthyl.

8. A compound of claim 1, wherein $R^3$ is H and $R^4$ is H, tert-butyl, tert-butoxymethyl, tetra-hydro-2-pyranyl, trialkylsilyl of a total of 3-6 C atoms, or alkanoyl of 2-6 C atoms.

9. A compound of claim 1, wherein D is a bond, —$CH_2$— or 1-pentin-1,4-ylene, $R^1$ is H or benzamidophenyl, $R^2$ is alkyl of 1-7 C atoms, phenyl, chlorophenyl or, when D is —$CH_2$—, also chlorophenoxy, $R^3$ is H, $R^4$ is H, tert-butyl, tert-butoxymethyl, tetrahydro-2-pyranyl, trialkylsilyl having a total of 3-6 C atoms, or alkanoyl of 2-6 C atoms, and $R^5$ is H or $CH_3$.

10. A compound of claim 1, wherein D is a bond, —$CH_2$— or 1-pentin-1,4-ylene, $R^1$ is H or p-benzamidophenyl, $R^2$ is methyl, pentyl, hexyl, 1-methylpentyl, 1-methylhexyl, pheny, o-chlorophenyl or, when D is —$CH_2$—, is also m-chlorophenoxy, $R^3$ is H, $R^4$ is H or tert-butyldimethylsilyl, and $R^5$ is H or $CH_3$.

11. A compound of claim 1, wherein D is a bond, $R^1$ is H or p-benzamidophenyl, $R^2$ is pentyl, hexyl, 1-methylpentyl or 1-methyl-hexyl, $R^3$ is H, $R^4$ is H or tert-butyldimethylsilyl, and $R^5$ is H or $CH_3$.

12. A compound of claim 1, wherein D is a bond or —$CH_2$—, $R^1$ is H or p-benzamidophenyl, $R^2$ is phenyl, o-chlorophenyl or, when D is —$CH_2$—, is also m-chlorophenoxy, $R^3$ is H, $R^4$ is H or tert-butyldimethylsilyl, and $R^5$ is H or $CH_3$.

13. A compound of claim 1, wherein D is a bond, $R^1$ is H or p-benzamidophenyl, $R^2$ is 1-methylhexyl, $R^3$ is H, $R^4$ is H, tert-butoxymethyl, tetrahydro-2-pyranyl, trialkylsilyl of a total of 3-6 C atoms, or alkanoyl of 2-6 C atoms, and $R^5$ is H.

14. A compound of claim 1, wherein D is a bond, $R^1$ is H or p-benzamidophenyl, $R^2$ is 1-methylhexyl, $R^3$ is H, $R^4$ is H or tert-butyldimethylsilyl, and $R^5$ is H.

15. A pharmaceutical composition comprising a compound of claim 1 and a pharmacologically acceptable carrier.

16. A composition of claim 15, wherein the amount of said compound in the composition is 0.1 to 100 mg.

17. A method of treating hypertension or cardiac insufficiency in a patient comprising administering a compound of claim 1 to the patient.

18. A method of inhibiting platelet aggregation in a patient comprising administering a compound of claim 1 to the patient.

19. A method of treating cardiac insufficiency in a patient comprising administering a compound of claim 1 to the patient.

* * * * *